US011007131B2

(12) United States Patent
Guerin et al.

(10) Patent No.: US 11,007,131 B2
(45) Date of Patent: *May 18, 2021

(54) DYEING COMPOSITION COMPRISING A DIRECT DYE OF TRIARYLMETHANE STRUCTURE, AND A SILICONE

(71) Applicant: L'OREAL, Paris (FR)

(72) Inventors: Frédéric Guerin, Paris (FR); Valérie Nicou, Clichy (FR); Maria Nieto, Saint Ouen (FR)

(73) Assignee: L'OREAL, Paris (FR)

( * ) Notice: Subject to any disclaimer, the term of this patent is extended or adjusted under 35 U.S.C. 154(b) by 189 days.

This patent is subject to a terminal disclaimer.

(21) Appl. No.: 16/063,805

(22) PCT Filed: Dec. 20, 2016

(86) PCT No.: PCT/EP2016/081982
§ 371 (c)(1),
(2) Date: Jun. 19, 2018

(87) PCT Pub. No.: WO2017/108828
PCT Pub. Date: Jun. 29, 2017

(65) Prior Publication Data
US 2020/0261337 A1    Aug. 20, 2020

(30) Foreign Application Priority Data

Dec. 21, 2015    (FR) ...................... 1562993

(51) Int. Cl.
| | | |
|---|---|---|
| *A61Q 5/10* | (2006.01) | |
| *A61K 8/41* | (2006.01) | |
| *A61K 8/898* | (2006.01) | |
| *A61Q 5/06* | (2006.01) | |

(52) U.S. Cl.
CPC .............. *A61K 8/411* (2013.01); *A61K 8/416* (2013.01); *A61K 8/898* (2013.01); *A61Q 5/065* (2013.01); *A61K 2800/432* (2013.01)

(58) Field of Classification Search
CPC ............ A61Q 5/065; A61K 2800/4322; A61K 2800/432; A61K 8/416; A61K 8/411; A61K 8/898; A61K 8/31; A61K 8/25; A61K 2800/5426; A61K 2800/4324
USPC .................................................... 8/405, 426
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,667,899 A | 6/1972 | Hartnett et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,157,388 A | 6/1979 | Christiansen |
| 4,165,367 A | 8/1979 | Chakrabarti |
| 4,172,887 A | 10/1979 | Vanlerberghe et al. |
| 4,185,087 A | 1/1980 | Morlino |

(Continued)

FOREIGN PATENT DOCUMENTS

| | | |
|---|---|---|
| DE | 10355743 A1 | 7/2005 |
| EP | 0080976 A1 | 6/1983 |

(Continued)

OTHER PUBLICATIONS

International Search Report for counterpart Application No. PCT/EP2016/081984, dated Feb. 3, 2017.
Porter, M.R., "Handbook of Surfactants," published by Blackie & Son (Glasgow and London), 1991, pp. 116-178.
Instituto Naturvita, "Auburn Hair Colour Hair Mask," Mintel, XP002760616, Feb. 2010.
Procter & Gamble, "Hair Colorant," Mintel, XP002760618, Sep. 2014.
Lorybel, "Intensive Care Combing Cream," Mintel, XP002760617, Nov. 2015.

(Continued)

*Primary Examiner* — Eisa B Elhilo
(74) *Attorney, Agent, or Firm* — The Marbury Law Group, PLLC

(57) ABSTRACT

The present invention relates to a composition for dyeing keratin fibres comprising, in a cosmetically acceptable medium: —one or more direct dyes of triarylmethane structure, —one or more amino silicones and—one or more surfactants. The invention also relates to a process for dyeing keratin fibres using said composition and also to a use for dyeing keratin fibres.

16 Claims, No Drawings

(56) References Cited

U.S. PATENT DOCUMENTS

| | | | |
|---|---|---|---|
| 4,197,865 A | 4/1980 | Jacquet et al. | |
| 4,217,914 A | 8/1980 | Jacquet et al. | |
| 4,237,243 A | 12/1980 | Quack et al. | |
| 4,240,450 A | 12/1980 | Grollier et al. | |
| 4,349,532 A | 9/1982 | Vanlerberghe et al. | |
| 4,509,949 A | 4/1985 | Huang et al. | |
| 4,591,610 A | 5/1986 | Grollier | |
| 4,702,906 A | 10/1987 | Jacquet et al. | |
| 4,719,282 A | 1/1988 | Nadolsky et al. | |
| 4,761,273 A | 8/1988 | Grollier et al. | |
| 4,839,166 A | 6/1989 | Grollier et al. | |
| 4,874,554 A | 10/1989 | Lange et al. | |
| 4,996,059 A | 2/1991 | Grollier et al. | |
| 5,089,252 A | 2/1992 | Grollier et al. | |
| 5,792,221 A | 8/1998 | Lagrange et al. | |
| 6,120,780 A | 9/2000 | Dupuis et al. | |
| 6,884,265 B2 | 4/2005 | Vidal et al. | |
| 7,060,110 B2 | 6/2006 | Vidal et al. | |
| 7,967,873 B1 | 6/2011 | Guthrie | |
| 2002/0053111 A1* | 5/2002 | Kravtchenko | A61Q 5/10 8/405 |
| 2002/0095732 A1 | 7/2002 | Kravtchenko et al. | |
| 2003/0106169 A1 | 6/2003 | Vidal et al. | |
| 2004/0078906 A1 | 4/2004 | Plos et al. | |
| 2004/0093675 A1 | 5/2004 | Vidal et al. | |
| 2004/0107513 A1 | 6/2004 | Vidal et al. | |
| 2004/0127692 A1 | 7/2004 | David et al. | |
| 2004/0143911 A1 | 7/2004 | Vidal | |
| 2004/0168263 A1 | 9/2004 | Vidal | |
| 2004/0200009 A1 | 10/2004 | Vidal | |
| 2004/0244123 A1 | 12/2004 | Vidal et al. | |
| 2005/0039268 A1 | 2/2005 | Plos et al. | |
| 2008/0227716 A1 | 9/2008 | Rothe et al. | |
| 2008/0311068 A1* | 12/2008 | Runglertkriangkrai | A61K 8/58 424/70.122 |

FOREIGN PATENT DOCUMENTS

| | | |
|---|---|---|
| EP | 0122324 A1 | 10/1984 |
| EP | 0173109 A2 | 3/1986 |
| EP | 0216479 A1 | 4/1987 |
| EP | 0337354 A1 | 10/1989 |
| EP | 0395282 A2 | 10/1990 |
| EP | 0503853 A2 | 9/1992 |
| EP | 0530974 A1 | 3/1993 |
| EP | 0714954 A2 | 6/1996 |
| EP | 0815828 A1 | 1/1998 |
| EP | 1175893 A2 | 1/2002 |
| FR | 1492597 A | 8/1967 |
| FR | 1583363 A | 10/1969 |
| FR | 2077143 A5 | 10/1971 |
| FR | 2080759 A1 | 11/1971 |
| FR | 2162025 A | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2416723 A1 | 9/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| FR | 2692572 A1 | 12/1993 |
| FR | 2807650 A1 | 10/2001 |
| FR | 2822693 A1 | 10/2002 |
| FR | 2822694 A1 | 10/2002 |
| FR | 2822696 A1 | 10/2002 |
| FR | 2822698 A1 | 10/2002 |
| FR | 2825625 A1 | 12/2002 |
| FR | 2829926 A1 | 3/2003 |
| FR | 2844269 A1 | 3/2004 |
| FR | 2825702 A1 | 12/2012 |
| GB | 1546809 A | 5/1979 |
| GB | 2117013 A | 10/1983 |
| GB | 2168082 A | 6/1986 |
| JP | 2001-106611 A | 4/2001 |
| WO | 95/01772 A1 | 1/1995 |
| WO | 95/15144 A1 | 6/1995 |
| WO | 98/44012 A1 | 10/1998 |
| WO | 02/078660 A1 | 10/2002 |
| WO | 02/100369 A1 | 12/2002 |
| WO | 02/100834 A1 | 12/2002 |
| WO | 2008/152595 A2 | 12/2008 |
| WO | 2017/108828 A1 | 6/2017 |

OTHER PUBLICATIONS

Mintel_Semi-Permanent_Colouring_Hydrating_Hair_Mask Lola Cosmetics, "Semi-Permanent Colouring Hydrating Hair Mask," Mintel, XP002760616, Mar. 2015.
Non-Final Office Action for copending U.S. Appl. No. 16/063,757, dated Jun. 23, 2020.
STIC Search Report dated Jun. 17, 2020.
Final Office Action for copending U.S. Appl. No. 16/063,757, dated Nov. 5, 2020.

* cited by examiner

DYEING COMPOSITION COMPRISING A DIRECT DYE OF TRIARYLMETHANE STRUCTURE, AND A SILICONE

CROSS REFERENCE TO RELATED APPLICATIONS

This is a national stage application of PCT/EP2016/081982, filed internationally on Dec. 20, 2016, which claims priority to French Application No. 1562993, filed on Dec. 21, 2015, both of which are incorporated by reference herein in their entireties.

The present invention relates to a composition for dyeing keratin fibres, in particular human keratin fibres such as the hair, comprising one or more dyes of triarylmethane structure, one or more amino silicones and one or more surfactants.

The invention also relates to a process for dyeing keratin fibres, and also to the use thereof for dyeing keratin fibres.

Many people have sought for a long time to modify the colour of their hair and in particular to mask their grey hair.

It is known practice to dye keratin fibres with dyeing compositions containing direct dyes. These compounds are coloured and colouring molecules that have affinity for the fibres. It is known practice, for example, to use direct dyes of the nitrobenzene type, anthraquinone or nitropyridine dyes, and dyes of the azo, xanthene, acridine, azine or triarylmethane type.

These dyes are usually applied to fibres optionally in the presence of an oxidizing agent if it is desired to obtain simultaneous lightening of the fibres. Once the leave-on time has elapsed, the fibres are rinsed, optionally washed and dried.

The colourings resulting from the use of direct dyes are colourings that are often chromatic but are, however, only temporary or semi-permanent since the nature of the interactions that bind the direct dyes to the keratin fibre and their desorption from the surface and/or the core of the fibre are responsible for their weak dyeing power and their poor relative persistence with respect to washing or perspiration. Thus, the colourings may also not be sufficiently fast in the face of external agents such as light, shampoos and perspiration.

It is known practice to use compounds of triarylmethane type to obtain a very chromatic keratin fibre colouring. However, it has been observed that their dyeing power is limited and sometimes insufficient for providing good intensity. Furthermore, it has been observed that the colourings obtained exhibit poor fastness with respect to washing, in particular on sensitized hair, in particular bleached hair.

The aim of the present invention is to provide a dyeing composition which results in good dyeing properties.

In particular, one of the aims of the present invention is to provide direct dyeing compositions that make it possible to obtain a strong, chromatic, aesthetic, sparingly selective colouring with varied shades, which shows good resistance to the various attacking factors to which the hair may be subjected, such as shampoos, light, sweat and permanent reshaping, and which can be faded out easily.

One particular objective of the invention is to provide compositions for dyeing hair that has previously been lightened.

This aim is achieved by means of the present invention, a subject of which is in particular a composition for dyeing keratin fibres such as the hair, comprising, in a cosmetically acceptable medium:

one or more direct dyes of triarylmethane structure which are preferably cationic,
one or more amino silicones, and
one or more surfactants.

The pH of the composition according to the invention is preferably acidic, preferably less than 5.

The applicant has thus discovered that formulating these direct dyes of triarylmethane structure in this specific support makes it possible to obtain a very good development of the colour, very strong colours, with, where appropriate, a decrease in selectivity and better fastness, in particular better fastness with respect to washing.

Moreover, the dyeing compositions according to the present invention make it possible to achieve a wide range of colours with varied shades.

In particular, the compositions in accordance with the invention make it possible to lead to satisfactory colour build-up, especially on depigmented keratin fibres, such as grey hair.

For the purposes of the present invention, the term "build-up" of the colour of keratin fibres is intended to mean the variation in colouring between locks of undyed grey hair and locks of dyed hair.

Other subjects, characteristics, aspects and advantages of the present invention will emerge even more clearly on reading the description and the examples that follow.

In that which follows and unless otherwise indicated, the limits of a range of values are included in this range.

The expression "at least one" is equivalent to the expression "one or more".

Direct Dye of Triarylmethane Structure:

The composition according to the invention comprises one or more direct dye(s) of triarylmethane structure.

Preferably, the total content of direct dye(s) of triarylmethane structure ranges from 0.0001% to 10% by weight, preferably from 0.0005% to 5% by weight and better still from 0.00075% to 3% by weight relative to the total weight of the composition.

In particular, the triarylmethane dye(s) of the invention may be anionic, cationic, neutral or zwitterionic.

Preferably, the dye(s) of the invention are chosen from the triarylmethane dyes of formula (I):

(I)

and also the organic or mineral, acid or base addition salts thereof, the geometrical isomers, optical isomers and tautomers thereof, and the mesomeric forms thereof, and the solvates such as hydrates;

in which formula (I), A, B and C are identical or different, and represent a (hetero)aryl group such as phenyl which is optionally substituted, ═══ represents a single bond or a double bond.

The direct dyes of formula (I) can thus be cationic, anionic, non-ionic or zwitterionic.

According to one particularly preferred embodiment of the invention, the triarylmethane dye(s) are cationic.

The term "cationic direct dye" is commonly intended to mean dyes referred to as "basic direct dyes" or "basic dyes" owing to their affinity with acidic substances.

The term "cationic direct dyes" is intended to mean any direct dye comprising in particular in its structure at least one endocyclic or exocyclic, cationic or cationizable group. In particular, the charge may be borne by an aryl or heteroaryl group.

Preferably, the triarylmethane direct dye(s) according to the invention are cationic dyes of formulae (IIa) and (II'a) below:

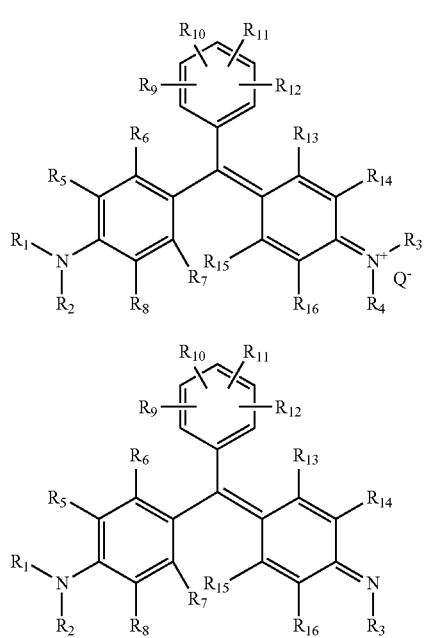

and also the organic or mineral, acid or base addition salts thereof, the geometrical isomers, optical isomers and tautomers thereof, and the mesomeric forms thereof, and the solvates thereof such as hydrates:

in which formulae (IIa) and (II'a) below:
R1, R2, R3 and R4, which may be identical or different, represent a hydrogen atom or a $(C_1-C_6)$alkyl group which is optionally substituted, preferably with a hydroxyl group, an aryl group such as phenyl, an aryl$(C_1-C_4)$alkyl group such as benzyl, a heteroaryl, or a heteroaryl$(C_1-C_4)$alkyl group, or else two groups R1 and R2, and/or R3 and R4, borne by the same nitrogen atom, form, together with the nitrogen atom which bears them, an optionally substituted heterocycloalkyl group such as morpholino, piperazino or piperidino; preferably, R1, R2, R3 and R4, which may be identical or different, represent a hydrogen atom or a $(C_1-C_4)$ alkyl group;
R5, R6, R7, R8, R9, R10, R11, R12, R13, R14, R15, and R16, which may be identical or different, represent a hydrogen atom, a halogen atom, or a group chosen from i) hydroxyl; ii) thiol; iii) amino; iv) (di)$(C_1-C_4)$(alkyl)amino; v) (di)arylamino such as (di)phenylamino; vi) nitro; vii) acylamino (—NR—C(O)R') in which the radical R is a hydrogen atom or a $C_1-C_4$ alkyl radical optionally bearing at least one hydroxyl group, and the radical R' is a $C_1-C_2$ alkyl radical; viii) carbamoyl ((R)2N—C(O)—) in which the radicals R, which may be identical or different, represent a hydrogen atom or a $C_1-C_4$ alkyl radical optionally bearing at least one hydroxyl group; ix) carboxylic acid or ester, (—O—C(O)R') or (—C(O)OR'), in which the radical R' is a hydrogen atom, or $C_1-C_4$ alkyl optionally bearing at least one hydroxyl group and the radical R' is a $C_1-C_2$ alkyl radical; x) alkyl optionally substituted in particular with a hydroxyl group; xi) alkylsulfonylamino (R'SO_2—NR—) in which the radical R represents a hydrogen atom or a $C_1-C_4$ alkyl radical optionally bearing at least one hydroxyl group and the radical R' represents a $C_1-C_4$ alkyl radical or a phenyl radical; xii) aminosulfonyl ((R)2N—SO_2—) in which the radicals R, which may be identical or different, represent a hydrogen atom or a $C_1-C_4$ alkyl radical optionally bearing at least one hydroxyl group; xiii) $(C_1-C_4)$alkoxy; and xiv) $(C_1-C_4)$alkylthio;
or else two radicals borne by two contiguous carbon atoms R5 and R6 and/or R7 and R8 and/or R9 and R10 and/or R11 and R12 and/or R13 and R14 and/or R15 and R16 form, together with the carbon atoms which bear them, an aryl or heteroaryl, preferably benzo, 6-membered fused ring cycle, said ring possibly also being optionally substituted, preferably an unsubstituted benzo ring;
Q- represents an anionic counterion for achieving electroneutrality, preferably chosen from halides such as chloride or bromide, and phosphate.

When the cationic dye comprises one or more anionic substituents such as COOR or $SO_3R$ with R denoting a hydrogen or a cation, it is understood that there are then more cationic substituents than anionic substituents, such that the overall resulting charge of the triarylmethane structure is cationic.

According to one preferred embodiment, the triarylmethane dye(s) of the invention is (are) chosen from those of formula (IIa) or (II'a), in which, taken together or separately,
R1, R2, R3 and R4 represent a hydrogen atom or a $(C_1-C_4)$alkyl group such as methyl or ethyl,
R5, R6, R7, R8, R9, R10, R11, R12, R13, R14, R15, and R16 represent a hydrogen atom, a halogen atom, such as chlorine, or a $(C_1-C_4)$alkyl group such as methyl or ethyl, an amino group, or a (di)$(C_1-C_4)$(alkyl)amino group, and preferably at least one of the groups R9, R10, R11 or R12 represents a hydrogen atom, a halogen atom (Cl), or an amino group, or a $(C_1-C_4)$(alkyl)amino or (di)$(C_1-C_4)$(alkyl)amino group, preferably in the position para to the phenyl group.

Preferably, the direct dye(s) of triarylmethane structure are chosen from Basic Violet 1, Basic Violet 2, Basic Violet 3, Basic Violet 4, Basic Violet 14, Basic Blue 1, Basic Blue 7, Basic Blue 26, Basic Green 1, Basic Blue 77 (also called HC Blue 15), and mixtures thereof.

The term "anionic counterion" is intended to mean an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1-C_6$ alkylsulfonates: Alk-S(O)_2O$^-$ such as methanesulfonate or mesylate and ethanesulfonate; iv) arylsulfonates: Ar—S(O)_2O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)_2O$^-$ such as methoxy sulfate and ethoxy sulfate; xii) aryloxy sulfates: Ar—O—S(O)_2O$^-$, xiii) phosphates O=P(OH)_2—O$^-$, O=P(O$^-$)_2—OH, O=P(O$^-$)_3, HO—[P(O)(O$^-$)]_w—P(O)(O$^-$)_2 with w being an integer; xiv) acetate; xv) triflate; and xvi) borates such as tetrafluoroborate, xvii) disulfate (O=)_2S(O$^-$)_2 or $SO_4^2$ and monosulfate $HSO_4$.

The anionic counterion, derived from an organic or mineral acid salt, ensures the electroneutrality of the molecule. Thus, it is understood that, when the anion comprises several anionic charges, then the same anion can be used for the electroneutrality of several cationic groups in the same molecule or else can be used for the electroneutrality of several molecules. For example, a disulfide dye of formula (I) which contains two cationic chromophores can either contain two "singly charged" anionic counterions or contains a "doubly charged" anionic counterion, such as $(O=)_2 S(O^-)_2$ or $O=P(O^-)_2$—OH.

The term "cationic counterion" is intended to mean alkali metal cations, alkaline-earth metal cations or organic cations such as ammoniums, preferably the anionic counterions of the invention are chosen from alkali metals such as $N^+$ or $K^+$.

A "cationic heteroaryl radical" is a heteroaryl group as defined above which comprises an endocyclic or exocyclic quaternized cationic group.

When the cationic charge is endocyclic, it is included in the electron delocalization via the mesomeric effect, for example it is a pyridinium, imidazolium or indolinium group:

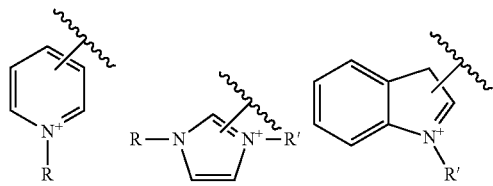

with R and R' being a heteroaryl substituent as defined above and particularly a (hydroxy)($C_1$-$C_8$)alkyl group such as methyl.

When the charge is exocyclic, for example, it involves an ammonium or phosphonium substituent R' such as trimethylammonium, which is outside the heteroaryl such as pyridyl, indolyl, imidazolyl or naphthalimidyl in question;

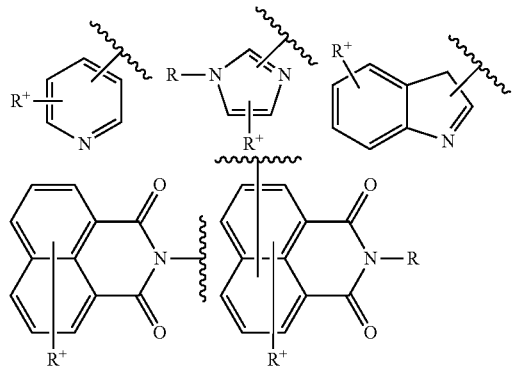

with R a heteroaryl substituent as defined above and R' an ammonium $RaRbRcN^+$—, phosphonium $RaRbRcP^+$ or ammonium $RaRbRcN^+$—$C_1$-$C_6$)alkylamino group with Ra, Rb and Rc, which are identical or different, representing a hydrogen atom or a ($C_1$-$C_8$)alkyl group, such as methyl.

A "cationic aryl carrying an exocyclic charge" is intended to mean an aryl ring of which the quaternized cationic group is outside said ring; it is especially an ammonium or phosphonium $R^+$ substituent, such as trimethylammonium, which is outside the aryl, such as phenyl or naphthyl:

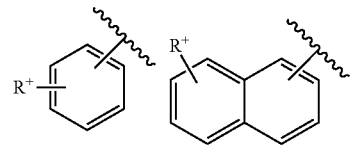

Preferably, the total content of cationic direct dye(s) of triarylmethane structure is between 0.0001% and 10% by weight, preferably between 0.0005% and 5% by weight and better still 0.00075% and 3% by weight relative to the total weight of the composition.

According to another embodiment, the dye(s) of triarylmethane structure is (are) chosen from anionic dyes of triarylmethane structure.

The term "anionic direct dyes" is intended to mean any direct dye comprising in its structure at least one sulfonate $SO_3$— group and/or at least one carboxylate group $C(O)O$— and optionally one or more anionic groups G- with G-, which may be identical or different, representing an anionic group chosen from alkoxide O—, thiolate S—, carboxylate and thiocarboxylate: C(Q)Q'-, with Q and Q', which may be identical or different, representing an oxygen or sulfur atom; preferably, G- represents a carboxylate, i.e. Q and Q' represents an oxygen atom.

In particular, the term "anionic direct dyes" is commonly intended to mean dyes referred to as "acid direct dyes" owing to their affinity with alkaline substances. The term "anionic direct dyes" is intended to mean any direct dye comprising in its structure at least one $CO_2R$ or $SO_3R$ substituent with R denoting a hydrogen atom or a cation originating from a metal or from an amine, or an ammonium ion.

When the anionic dye comprises one or more cationic substituents, it is understood that there are then more anionic substituents than cationic substituents, such that the overall resulting charge of the triarylmethane structure is anionic.

A group is said to be "bearing a quaternizable cationic group" when it comprises at least one tertiary amine or tertiary phosphine at the end of a hydrocarbon-based chain, preferably $C_1$-$C_{10}$ alkyl, such as —(CR'R")p-N(Ra)—Rb with R' and R", which may be identical or different, representing a hydrogen atom or a ($C_1$-$C_6$) alkyl group; Ra and Rb, which may be identical or different, representing a (poly)(hydroxy)($C_1$-$C_6$)alkyl group or Ra and Rb form, together with the nitrogen atom that bears them, a heterocycloalkyl group such as morpholino, piperidino or piperazino; and p representing an integer between 1 and 10 inclusive; preferably, R' and R" represent a hydrogen atom, Ra and Rb represent a ($C_1$-$C_4$)alkyl group and p is between 2 and 5.

The "aryl" or "heteroaryl" radicals or the aryl or heteroaryl part of a radical may be substituted with at least one substituent borne by a carbon atom, chosen from:

a $C_1$-$C_{16}$, preferably $C_1$-$C_8$, alkyl radical optionally substituted with one or more radicals chosen from the radicals hydroxyl, $C_1$-$C_2$ alkoxy, $C_2$-$C_4$ (poly)hydroxyalkoxy, acylamino or amino substituted with two identical or different $C_1$-$C_4$ alkyl radicals which optionally bear at least one hydroxyl group or it being possible for the two radicals to form, with the nitrogen atom to which they are attached, a saturated or unsaturated and optionally substituted 5- to 7-membered and preferably 5- or 6-membered heterocycle optionally comprising another nitrogen or non-nitrogen heteroatom;

a halogen atom such as chlorine, fluorine or bromine;

a hydroxyl group;

a $C_1$-$C_2$ alkoxy radical;

a (poly)hydroxy($C_2$-$C_4$)alkoxy radical;

an amino radical;

nitro;

a 5- or 6-membered heterocycloalkyl radical;

an optionally cationic 5- or 6-membered heteroaryl radical, preferentially imidazolium, optionally substituted with a ($C_1$-$C_4$)alkyl radical, preferentially methyl;

an amino radical substituted with one or two identical or different $C_1$-$C_6$ alkyl radicals, optionally bearing at least:

a hydroxyl group, an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom, an acylamino (—NR—C(O)R') radical in which the R radical is a hydrogen atom or a $C_1$-$C_4$ alkyl radical optionally bearing at least one hydroxyl group and the R' radical is a $C_1$-$C_2$ alkyl radical;

a carbamoyl ((R)2N—C(O)—) radical in which the R radicals, which may be identical or different, represent a hydrogen atom or a $C_1$-$C_4$ alkyl radical optionally bearing at least one hydroxyl group;

a carboxylic acid or ester radical, (—O—C(O)R') or (—C(O)OR'), in which the radical R' is a hydrogen atom or a $C_1$-$C_4$ alkyl radical optionally bearing at least one hydroxyl group, and the radical R' is a $C_1$-$C_2$ alkyl radical;

the carboxylic radical possibly being in acid or salified form (preferably with an alkali metal or a substituted or unsubstituted ammonium);

an alkylsulfonylamino radical (R'SO$_2$—NR—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

an aminosulfonyl radical ((R)2N—SO$_2$—) radical in which the R radicals, which may be identical or different, represent a hydrogen atom or a $C_1$-$C_4$ alkyl radical optionally bearing at least one hydroxyl group;

(O)$_2$S(O)—, M+ with M+ representing a hydrogen atom or a cationic counterion;

(O)CO$^-$—, M$^+$ with M$^+$ as defined previously;

a cyano group (CN);

a (poly)haloalkyl group, preferably trifluoromethyl (CF$_3$).

The cyclic or heterocyclic part of a non-aromatic radical may be substituted with at least one substituent borne by a carbon atom, chosen from the groups:

hydroxyl, $C_1$-$C_4$ alkoxy or $C_2$-$C_4$ (poly)hydroxyalkoxy;

alkylcarbonylamino ((RC(O)—NR'—) in which the radical R' is a hydrogen atom, or a $C_1$-$C_4$ alkyl radical optionally bearing at least one hydroxyl group and the radical R is a $C_1$-$C_2$ alkyl radical or an amino radical substituted with two identical or different $C_1$-$C_4$ alkyl groups optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy ((RC(O)—O—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming, with the nitrogen atom to which they are attached, a saturated or unsaturated, optionally substituted 5- to 7-membered heterocycle, optionally comprising at least one other nitrogen or non-nitrogen heteroatom;

alkoxycarbonyl ((RO—C(O)—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming, with the nitrogen atom to which they are attached, a saturated or unsaturated, optionally substituted 5- to 7-membered heterocycle, optionally comprising at least one other nitrogen or non-nitrogen heteroatom.

A cyclic or heterocyclic radical or a non-aromatic part of an aryl or heteroaryl radical may also be substituted with one or more oxo groups.

An "aryl" radical represents a monocyclic or fused or non-fused polycyclic group comprising from 6 to 22 carbon atoms, at least one ring of which is aromatic; the aryl radical is in particular a phenyl, biphenyl, naphthyl, indenyl, anthracenyl or tetrahydronaphthyl and more preferably phenyl.

A "heteroaryl" radical represents a 5- to 22-membered, monocyclic or fused or non-fused polycyclic group, comprising from 1 to 6 heteroatoms chosen from nitrogen, oxygen, sulfur and selenium atoms, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof.

A "cyclic" radical is a "cycloalkyl" radical, i.e. a non-aromatic monocyclic or fused or non-fused polycyclic radical containing from 5 to 22 carbon atoms, which may comprise one or more unsaturations, such as cyclohexyl or cyclopentyl.

A "heterocyclic" radical is a non-aromatic, monocyclic or polycyclic, fused or non-fused 5- to 22-membered radical, comprising from 1 to 6 heteroatoms chosen from nitrogen, oxygen, sulfur and selenium atoms, morpholinyl, thiomorpholinyl, piperidyl, piperazinyl, pyrrolidinyl, tetrahydrofuranyl, tetrahydrothiophenyl, azepanyl, thioazepanyl; preferentially pyrrolidinyl and morpholino.

An "alkyl" radical is a linear or branched $C_1$-$C_{16}$, preferably $C_1$-$C_8$ and particularly $C_1$-$C_4$ hydrocarbon-based radical, such as methyl or ethyl.

An "alkenyl" radical is a linear or branched $C_2$-$C_{20}$ hydrocarbon-based radical comprising one or more conjugated or unconjugated double bonds, in particular a linear or branched $C_4$-$C_{10}$ radical comprising one, two or three double bonds, preferentially only one double bond.

The term "optionally substituted" attributed to the alkyl radical implies that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom.

An "alkoxy" radical is an alkyl-oxy or alkyl-O— radical for which the alkyl radical is a linear or branched $C_1$-$C_{16}$, preferentially $C_1$-$C_8$, particularly $C_1$-$C_4$ hydrocarbon-based radical such as methoxy or ethoxy, and when the alkoxy group is optionally substituted, this implies that the alkyl group is optionally substituted as defined above.

A "(poly)haloalkyl" radical is an "alkyl" radical as defined above, in which one or more hydrogen atoms are substituted or replaced with one or more halogen atoms such as the fluorine, chlorine or bromine atom; a polyhaloalkyl that may be mentioned is the trifluoromethyl group.

An "alkylthio" radical is an alkyl-S— radical for which the alkyl radical is a linear or branched $C_1$-$C_{16}$, preferentially $C_1$-$C_8$, particularly $C_1$-$C_4$ hydrocarbon-based radical such as methylthio or ethylthio, and when the alkylthio group is optionally substituted, this implies that the alkyl group is optionally substituted as defined above.

A cationic counterion is organic or mineral and preferentially chosen from alkali metal or alkaline-earth metal cations such as Na, Mg, K and Ca, and organic cations such as ammonium $NH_4^+$.

In particular, the anionic direct dye(s) are chosen from the triarylmethane dyes of formulae (IIb) and (II'b):

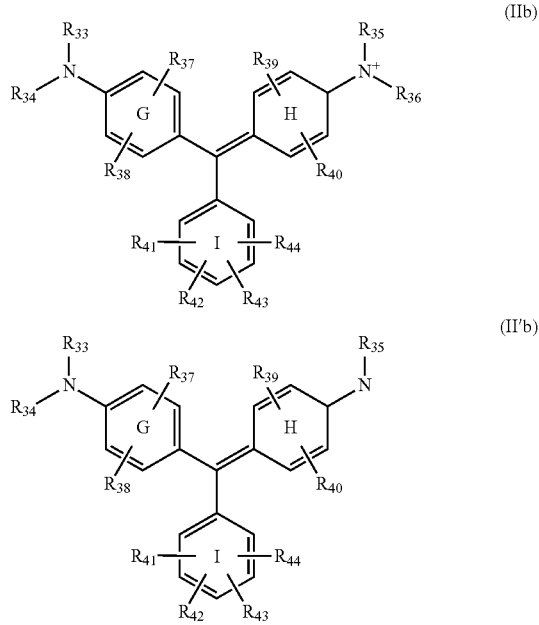

in which formulae (IIb) and (II'b):

R33, R34, R35 and R36, which may be identical or different, represent a hydrogen atom or a group chosen from alkyl, optionally substituted aryl and optionally substituted arylalkyl; particularly an alkyl group and benzyl optionally substituted with a group $(O)mS(O^-)$—, M+ with M+ and m as defined previously;

R37, R38, R39, R40, R41, R42, R43 and R44, which may be identical or different, represent a hydrogen atom or a group chosen from:

alkyl;
alkoxy, alkylthio;
amino, (di)(alkyl)amino;
hydroxyl, mercapto;
nitro, nitroso;
$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, M+ with M+ representing a hydrogen atom or a cationic counterion;
$(O)CO^-$—, M+ with M+ as defined previously;
or alternatively two contiguous groups R41 with R42 or R42 with R43 or R43 with R44 together form a fused benzo group: I'; with I' optionally substituted with one or more groups chosen from i) nitro; ii) nitroso; iii) $(O)2S(O^-)$—, M+; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; with M+, $R^o$, X, X', X" as defined previously.

Particularly, R37 to R40 represent a hydrogen atom, and R41 to R44, which may be identical or different, represent a hydroxyl group or $(O)2S(O^-)$—, M+; and when R43 with R44 together form a benzo group, it is preferentially substituted with a group $(O)2S(O^-)$—;

it being understood that at least one of the rings G, H, I or I' comprises at least one sulfonate radical $(O)2S(O^-)$— or a carboxylate radical —C(O)O—; preferentially sulfonate.

As examples of dyes of formulae (IIb) and (II'b), mention may be made of: Acid Blue 1; Acid Blue 3; Acid Blue 7, Acid Blue 9; Acid Violet 49, Acid Green 3, Acid Green 5 and Acid Green 50.

According to one particular embodiment, the triarylmethane dye(s) of the invention are fluorescent.

The term "fluorescent dye" is intended to mean a dye as defined previously, which, besides being coloured, is fluorescent, i.e. it has the capacity of re-emitting at least part of the light absorbed in the visible range at a wavelength longer than that absorbed. In particular, the fluorescent dye is capable of absorbing in the UV or visible radiation range at a wavelength λabs of between 250 and 800 nm and capable of re-emitting in the visible range at an emission wavelength λem of between 400 and 800 nm. Preferably, the fluorescent dye is a dye in the orange-colour range.

According to the present invention, the term "dye" is intended to mean a compound which has the capacity of colouring and which is in the form of a coloured compound that may be observed with the naked eye, i.e. absorbing light at a wavelength between the UV and visible radiation range, at a wavelength λabs of between 250 and 800 nm, particularly in the visible spectrum between 400 and 700 nm.

Preferably, the dyes of the invention are dyes which absorb in the violet and/or blue range, i.e. at an absorption wavelength which is included in the blue-violet range, particularly between 550 and 700 nm, more particularly between 580 and 680 nm.

According to one particular embodiment, when the triarylmethane dye(s) is (are) chosen from dyes which absorb in the blue and/or violet range, the composition may also comprise at least one additional direct dye (which may or may not be a triarylmethane), preferably which absorbs in the orange or red range, preferably in the red range, such as, for example, Acid Red 92.

Preferably, the dyes of triarylmethane structure are chosen from Basic Violet 2, Basic Blue 1 and/or Basic Blue 77 (also known as HC Blue 15), and mixtures thereof, better still from Basic Violet 2 and/or Basic Blue 77 (also known as HC Blue 15), and mixtures thereof.

Amino Silicone

The composition according to the invention comprises one or more amino silicones. The term "amino silicone" denotes any silicone comprising at least one primary, secondary or tertiary amine or a quaternary ammonium group.

The weight-average molecular masses of these amino silicones may be measured by gel permeation chromatography (GPC) at ambient temperature (25° C.), as polystyrene equivalents. The columns used are μ styragel columns. The eluent is THF and the flow rate is 1 ml/min. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

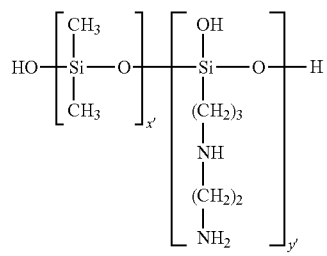

(A)

in which x' and y' are integers such that the weight-average molecular weight (Mw) is between 5000 and 500 000 approximately;

b) the amino silicones corresponding to formula (B):

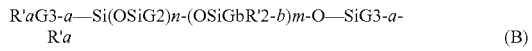

R'aG3-a—Si(OSiG2)n-(OSiGbR'2-b)m-O—SiG3-a-R'a    (B)

in which:

G, which may be identical or different, denotes a hydrogen atom or a phenyl, OH or $C_1$-$C_8$ alkyl group, for example methyl, or a $C_1$-$C_8$ alkoxy, for example methoxy, a, which may be identical or different, denotes 0 or an integer from 1 to 3, in particular 0, b denotes 0 or 1, in particular 1, m and n are numbers such that the sum (n+m) ranges from 1 to 2000, in particular from 50 to 150, it being possible for n to denote a number from 0 to 1999 and especially from 49 to 149, and for m to denote a number from 1 to 2000 and especially from 1 to 10;

R', which may be identical or different, denotes a monovalent radical of formula —CqH2qL in which q is a number ranging from 2 to 8 and L is an optionally quaternized amino group chosen from the following groups:

—N(R")2; —N+(R")3 A-; —NR"-Q-N(R")2 and —NR"-Q-N+(R")3 A-, in which R", which may be identical or different, denotes hydrogen, phenyl, benzyl, or a saturated monovalent hydrocarbon-based radical, for example a $C_1$-$C_{20}$ alkyl radical; Q denotes a linear or branched CrH2r group, r being an integer ranging from 2 to 6, preferably from 2 to 4; and A- represents a cosmetically acceptable anion, especially a halide such as fluoride, chloride, bromide or iodide.

Preferably, the amino silicones are chosen from the amino silicones of formula (B). Preferably, the amino silicones of formula (B) are chosen from amino silicones corresponding to formulae (C), (D), (E), (F) and/or (G) below.

According to a first embodiment, the amino silicones corresponding to formula (B) are chosen from silicones known as "trimethylsilyl amodimethicone", corresponding to formula (C):

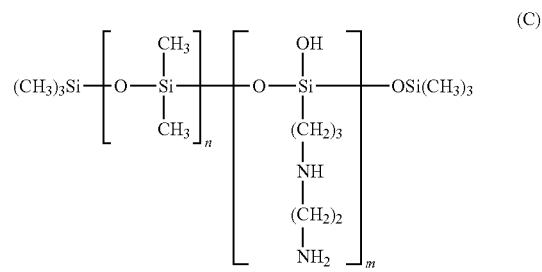

in which m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10.

According to a second embodiment, the amino silicones corresponding to formula (B) are chosen from the silicones of formula (D) below:

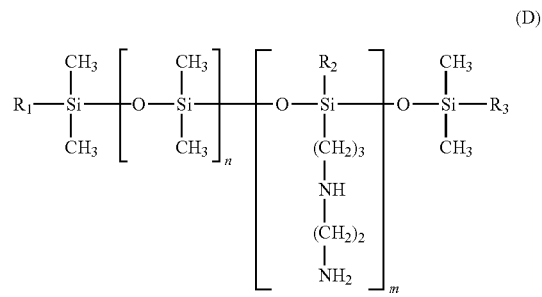

in which:

m and n are numbers such that the sum (n+m) ranges from 1 to 1000 and in particular from 50 to 250 and more particularly from 100 to 200; it being possible for n to denote a number from 0 to 999 and in particular from 49 to 249 and more particularly from 125 to 175, and for m to denote a number from 1 to 1000 and in particular from 1 to 10, and more particularly from 1 to 5;

R1, R2 and R3, which may be identical or different, represent a hydroxyl or $C_1$-$C_4$ alkoxy radical, at least one of the radicals R1 to R3 denoting an alkoxy radical.

Preferably, the alkoxy radical is a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular mass (Mw) of these silicones preferably ranges from 2000 to 1 000 000 and more particularly from 3500 to 200 000.

According to a third embodiment, the amino silicones corresponding to formula (B) are chosen from the silicones of formula (E) below:

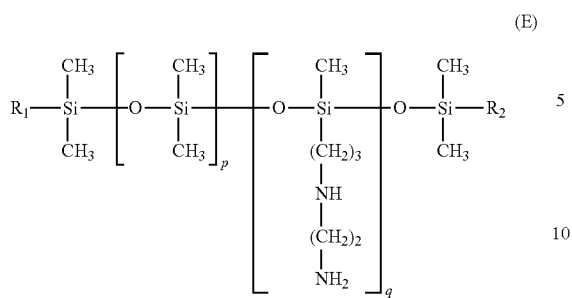

(E)

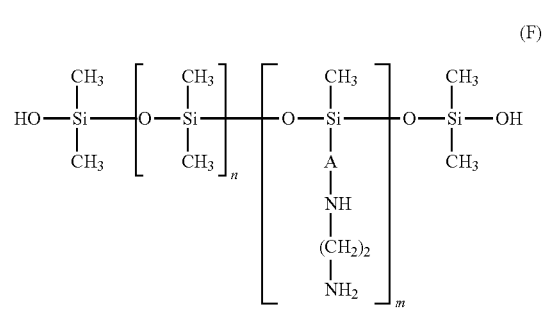

(F)

in which:

p and q are numbers such that the sum (p+q) ranges from 1 to 1000, in particular from 50 to 350 and more particularly from 150 to 250; it being possible for p to denote a number from 0 to 999 and especially from 49 to 349 and more particularly from 159 to 239, and for q to denote a number from 1 to 1000, especially from 1 to 10 and more particularly from 1 to 5;

R1 and R2, which are different, represent a hydroxyl or C1-C4 alkoxy radical, at least one of the radicals R1 or R2 denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly equals 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones of which the structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants can be of any nature but are preferably cationic and/or non-ionic. The numerical mean size of the silicone particles in the emulsion generally ranges from 3 nm to 500 nm. Preferably, especially as amino silicones of formula (E), use is made of microemulsions of which the mean particle size ranges from 5 nm to 60 nm (limits inclusive) and more particularly from 10 nm to 50 nm (limits inclusive). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

in which:

m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

A silicone corresponding to this formula is, for example, the Xiameter MEM 8299 Emulsion from Dow Corning.

According to a fifth embodiment, the amino silicones corresponding to formula (B) are chosen from the silicones of formula (G) below:

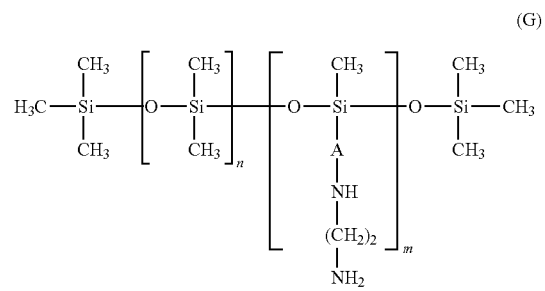

(G)

in which:

m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning;

c) the amino silicones corresponding to formula (H):

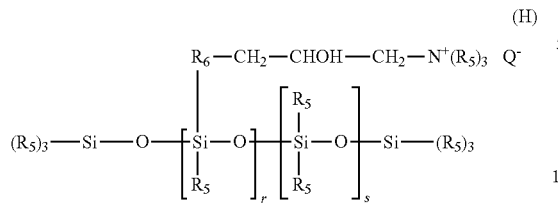
(H)

in which:
R5 represents a monovalent hydrocarbon-based radical containing from 1 to 18 carbon atoms, and in particular a $C_1$-$C_{18}$ alkyl or $C_2$-$C_{18}$ alkenyl radical, for example methyl;
R6 represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;
Q- is an anion such as a halide ion, especially chloride, or an organic acid salt, especially acetate;
r represents a mean statistical value ranging from 2 to 20 and in particular from 2 to 8;
s represents a mean statistical value ranging from 20 to 200 and in particular from 20 to 50.

Such amino silicones are especially described in U.S. Pat. No. 4,185,087;

d) the quaternary ammonium silicones of formula (I):

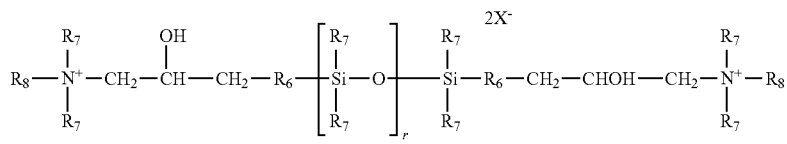
(I)

in which:
$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

R6 represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;

R8, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —R6-NHCOR7;

X— is an anion such as a halide ion, especially chloride, or an organic acid salt, especially acetate;

r represents a mean statistical value ranging from 2 to 200 and in particular from 5 to 100.

These silicones are described, for example, in Application EP-A-0 530 974;

e) the amino silicones of formula (J):

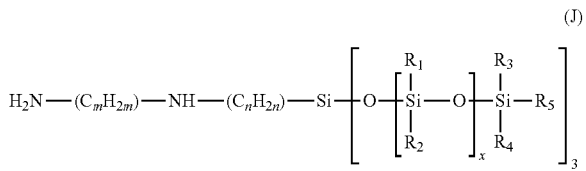
(J)

in which:
R1, R2, R3 and R4, which may be identical or different, denote a $C_1$-$C_4$ alkyl radical or a phenyl group,
R5 denotes a $C_1$-$C_4$ alkyl radical or a hydroxyl group,
n is an integer ranging from 1 to 5,
m is an integer ranging from 1 to 5, and
x is chosen such that the amine number ranges from 0.01 to 1 meq/g;

f) the multiblock polyoxyalkylenated amino silicones, of the type (AB)n, A being a polysiloxane block and B being a polyoxyalkylene block comprising at least one amine group.

Said silicones preferably are constituted of repeating units of the following general formulae:

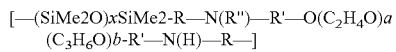

or alternatively

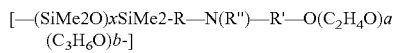

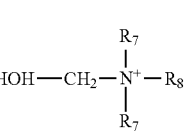

in which:
a is an integer greater than or equal to 1, preferably ranging from 5 to 200 and more particularly ranging from 10 to 100;
b is an integer between 0 and 200, preferably ranging from 4 to 100 and more particularly between 5 and 30;
x is an integer ranging from 1 to 10 000 and more particularly from 10 to 5000;
R" is a hydrogen atom or a methyl;
R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;
R', which may be identical or different, represent a linear or branched $C_2$-$C_{12}$ divalent hydrocarbon-based radical, optionally comprising one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially, R' denotes —$CH(CH_3)$—$CH_2$—.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000. Mention may be made especially of the silicones sold under the names Silsoft A-843 or Silsoft A+ by Momentive;

g) and mixtures thereof.

Preferably, the amino silicones are chosen from amino silicones of formula (B), preferentially from the amino silicones of formula (F).

The composition according to the invention may preferably comprise the amino silicone(s) in an amount ranging from 0.01% to 10% by weight, preferably from 0.1% to 5% by weight and better still from 0.5% to 3% by weight, relative to the total weight of the composition.

Surfactant

The composition according to the present invention also comprises one or more surfactants, said surfactants possibly being chosen from anionic surfactants, amphoteric or zwitterionic surfactants, non-ionic surfactants and cationic surfactants.

The term "anionic surfactant" is intended to mean a surfactant comprising as ionic or ionizable groups only anionic groups. These anionic groups are preferably chosen from the groups $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, POH and $PO^-$.

As examples of anionic surfactants that may be used in the composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N—($C_1$-$C_4$)alkyl N-acyltaurates, salts of alkyl monoesters of polyglycoside-polycarboxylic acids, acyllactylates, D-galactoside uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds (unless otherwise mentioned) generally comprising from 6 to 24 carbon atoms and the aryl group generally denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants that are optionally present may be mild anionic surfactants, i.e. anionic surfactants without a sulfate function.

Mention may in particular be made, as regards the mild anionic surfactants, of the following compounds and their salts, and also mixtures thereof:
polyoxyalkylenated alkyl ether carboxylic acids;
polyoxyalkylenated alkylaryl ether carboxylic acids;
polyoxyalkylenated alkylamido ether carboxylic acids, in particular those comprising 2 to 50 ethylene oxide groups;
alkyl-D-galactosideuronic acids;
acyl sarcosinates, acyl glutamates; and
alkylpolyglycoside carboxylic esters.

Use may be made most particularly of polyoxyalkylenated carboxylic acid alkyl ethers, for instance carboxylic acid lauryl ether (4.5 OE) sold, for example, under the name Akypo RLM 45 CA from Kao.

The amphoteric or zwitterionic surfactant(s) that may be used in the present invention may especially be optionally quaternized secondary or tertiary aliphatic amine derivatives, in which the aliphatic group is a linear or branched chain containing from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, sulfobetaines, ($C_8$-$C_{20}$)alkylamido($C_3$-$C_8$)alkylbetaines or ($C_8$-$C_{20}$)alkylamido($C_6$-$C_8$)-alkylsulfobetaines.

Among the optionally quaternized secondary or tertiary aliphatic amine derivatives that may be used, as defined above, mention may also be made of the compounds of respective structures ($A_1$), ($A_2$) and ($A_3$) below:

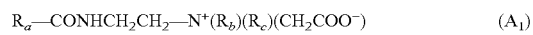

$$R_a\text{—CONHCH}_2\text{CH}_2\text{—N}^+(R_b)(R_c)(\text{CH}_2\text{COO}^-) \quad (A_1)$$

in which:

$R_a$ represents a $C_{10}$-$C_{30}$ alkyl or alkenyl group derived from an acid $R_a$—COOH preferably present in hydrolyzed coconut oil, or a heptyl, nonyl or undecyl group, $R_b$ represents a β-hydroxyethyl group, and $R_c$ represents a carboxymethyl group;

and

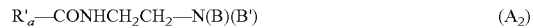

$$R'_a\text{—CONHCH}_2\text{CH}_2\text{—N(B)(B')} \quad (A_2)$$

in which:

B represents —$CH_2CH_2OX'$,

B' represents —$(CH_2)_z$—Y', with z=1 or 2,

X' represents the —$CH_2$—COOH, —$CH_2$—COOZ', —$CH_2CH_2$—COOH or —$CH_2CH_2$—COOZ' group or a hydrogen atom, Y' represents —COOH, —COOZ', or the group —$CH_2$—CHOH—$SO_3H$ or $CH_2$—CHOH—$SO_3Z'$, Z' represents an ion resulting from an alkali metal or alkaline-earth metal, such as sodium, an ammonium ion or an ion resulting from an organic amine, $R_a'$ represents a $C_{10}$-$C_{30}$ alkyl or alkenyl group of an acid $R_a'$—COOH preferably present in hydrolyzed coconut oil or in hydrolyzed linseed oil, an alkyl group, in particular a $C_{17}$ alkyl group and its iso form, or an unsaturated $C_{17}$ group.

These compounds of formula ($A_1$) or ($A_2$) are classified in the CTFA dictionary, 5th edition, 1993, under the names disodium cocoamphodiacetate, disodium lauroamphodiacetate, disodium caprylamphodiacetate, disodium caproamphodiacetate, disodium cocoamphodipropionate, disodium lauroamphodipropionate, disodium caprylamphodipropionate, disodium caproamphodipropionate, lauroamphodipropionic acid, cocoamphodipropionic acid.

By way of example, mention may be made of the cocoamphodiacetate sold by the company Rhodia under the trade name Miranol® C2M Concentrate.

in which formula:

Y" represents the group —COOH, —COOZ", —CH$_2$—CH(OH)SO$_3$H or the group —CH$_2$CH(OH)SO$_3$—Z";

R$_d$ and R$_e$, independently of each other, represent a C$_1$-C$_4$ alkyl or hydroxyalkyl radical;

Z" represents a cationic counterion derived from an alkali metal or alkaline-earth metal, such as sodium, an ammonium ion or an ion derived from an organic amine;

R$_a$" represents a C$_{10}$-C$_{30}$ alkyl or alkenyl group of an acid R$_a$"—COOH which is preferably present in hydrolyzed coconut oil or in hydrolyzed linseed oil;

n and n' denote, independently of each other, an integer ranging from 1 to 3.

Among the compounds of formula (A$_3$), mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use (C$_8$-C$_{20}$ alkyl)betaines such as cocoylbetaine, (C$_8$-C$_{20}$ alkyl)amido(C$_3$-C$_8$ alkyl)betaines such as cocoylamidopropylbetaine, and mixtures thereof. More preferentially, the amphoteric or zwitterionic surfactant(s) are chosen from cocoylamidopropylbetaine and cocoylbetaine.

The non-ionic surfactant(s) in the compositions of the present invention are especially described, for example, in the Handbook of Surfactants by M. R. Porter, published by Blackie & Son (Glasgow and London), 1991, pp. 116-178. They are especially chosen from fatty alcohols, fatty α-diols, fatty (C$_1$-C$_{20}$)alkylphenols and fatty acids, these compounds being ethoxylated, propoxylated or glycerolated and containing at least one fatty chain comprising, for example, from 8 to 18 carbon atoms, the number of ethylene oxide or propylene oxide groups possibly ranging especially from 1 to 200, and the number of glycerol groups possibly ranging especially from 1 to 30.

Mention may also be made of condensates of ethylene oxide and of propylene oxide with fatty alcohols, ethoxylated fatty amides preferably having from 1 to 30 ethylene oxide units, polyglycerolated fatty amides comprising on average from 1 to 5 glycerol groups, and in particular from 1.5 to 4, ethoxylated fatty acid esters of sorbitan containing from 1 to 30 ethylene oxide units, fatty acid esters of sucrose, fatty acid esters of polyethylene glycol, (C$_6$-C$_{24}$ alkyl)polyglycosides, oxyethylenated plant oils, N—(C$_6$-C$_{24}$ alkyl)glucamine derivatives, amine oxides such as (C$_{10}$-C$_{14}$ alkyl)amine oxides or N—(C$_{10}$-C$_{14}$ acyl)aminopropylmorpholine oxides.

The cationic surfactant(s) that may be used in the composition according to the invention are generally chosen from optionally polyoxyalkylenated primary, secondary or tertiary fatty amine salts, quaternary ammonium salts, and mixtures thereof.

Mention may in particular be made, as quaternary ammonium salts, for example, of:

those corresponding to the general formula (X) below:

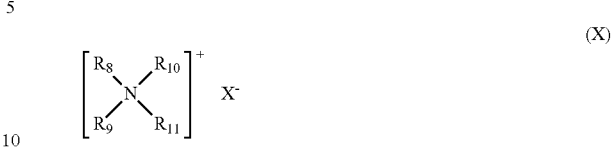

in which the groups R$_8$ to R$_{11}$, which may be identical or different, represent a linear or branched aliphatic group comprising from 1 to 30 carbon atoms or an aromatic group, such as aryl or alkylaryl, at least one of the groups R$_8$ to R$_{11}$ comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from C$_1$-C$_{30}$ alkyl, C$_1$-C$_{30}$ alkoxy, polyoxy(C$_2$-C$_6$)alkylene, C$_1$-C$_{30}$ alkylamide, (C$_{12}$-C$_{22}$)alkylamido(C$_2$-C$_6$)alkyl, (C$_{12}$-C$_{22}$)alkyl acetate and C$_1$-C$_{30}$ hydroxyalkyl groups; X$^-$ is an anion chosen from the group of halides, phosphates, acetates, lactates, (C$_1$-C$_4$)alkyl sulfates, and (C$_1$-C$_4$)alkylsulfonates or (C$_1$-C$_4$)alkylarylsulfonates.

Preference is given, among the quaternary ammonium salts of formula (X), on the one hand, to tetraalkylammonium chlorides, such as, for example, dialkyldimethylammonium or alkyltrimethylammonium chlorides in which the alkyl group comprises approximately from 12 to 22 carbon atoms, in particular behenyltrimethylammonium chloride, distearyldimethylammonium chloride, cetyltrimethylammonium chloride or benzyldimethylstearylammonium chloride, or also, on the other hand, to distearoylethylhydroxyethylmethylammonium methosulfate, dip almito ylethylhydroxyethylammo nium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (XI) below:

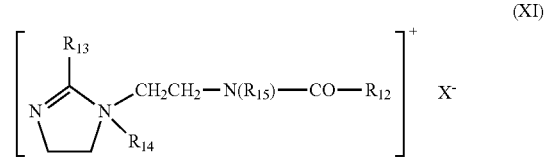

in which

R$_{12}$ represents an alkenyl or alkyl group comprising from 8 to 30 carbon atoms, for example derived from tallow fatty acids, R$_{13}$ represents a hydrogen atom, a C$_1$-C$_4$ alkyl group or an alkenyl or alkyl group comprising from 8 to 30 carbon atoms, R$_{14}$ represents a C$_1$-C$_4$ alkyl group, R$_{15}$ represents a hydrogen atom, a C$_1$-C$_4$ alkyl group, X$^-$ is an anion chosen from the group of halides, phosphates, acetates, lactates, (C$_1$-C$_4$)alkyl sulfates and (C$_1$-C$_4$)alkyl- or (C$_1$-C$_4$)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, particularly of formula (XII) below:

$$\left[ R_{16} - \underset{\underset{R_{18}}{\overset{\overset{R_{17}}{|}}{N}}}{} - (CH_2)_3 - \underset{\underset{R_{20}}{\overset{\overset{R_{19}}{|}}{N}}}{} - R_{21} \right]^{2+} \quad 2X^- \quad (XII)$$

in which $R_{16}$ denotes an alkyl group comprising approximately from 16 to 30 carbon atoms, which is optionally hydroxylated and/or interrupted with one or more oxygen atoms, $R_{17}$ is chosen from hydrogen, an alkyl group comprising from 1 to 4 carbon atoms or a group —$(CH_2)_3$—$N^+(R_{16a})(R_{17a})(R_{18a})$, $R_{16a}$, $R_{17a}$, $R_{18a}$, $R_{18}$, $R_{19}$, $R_{20}$ and $R_{21}$, which may be identical or different, are chosen from hydrogen or an alkyl group comprising from 1 to 4 carbon atoms, and $X^-$ is an anion chosen from the group of halides, acetates, phosphates, nitrates, $(C_1\text{-}C_4)$alkyl sulfates, $(C_1\text{-}C_4)$alkyl- or $(C_1\text{-}C_4)$alkylarylsulfonates, in particular methyl sulfate and ethyl sulfate.

Such compounds are, for example, Finquat CT-P, available from Finetex (Quaternium 89), and Finquat CT, available from Finetex (Quaternium 75);

quaternary ammonium salts comprising one or more ester functional groups, such as those of formula (XIII) below:

$$R_{24} - \overset{\overset{O}{\|}}{C} - (O - C_rH_{2r}(OH)_{r1})_y - \underset{\underset{R_{22}}{|}}{\overset{\overset{(C_sH_{2s}O)_z - R_{25}}{|}}{N^+}} - (C_tH_{2t}(OH)_{t1} - O)_x - R_{23} \quad X^- \quad (XIII)$$

in which:

$R_{22}$ is chosen from $C_1\text{-}C_6$ alkyl groups and $C_1\text{-}C_6$ hydroxyalkyl or dihydroxyalkyl groups, $R_{23}$ is chosen from:

the group $$R_{26} - \overset{\overset{O}{\|}}{C} -,$$

saturated or unsaturated, linear or branched $C_1\text{-}C_{22}$ hydrocarbon-based groups $R_{27}$, a hydrogen atom, $R_{25}$ is chosen from:

the group $$R_{28} - \overset{\overset{O}{\|}}{C} -,$$

saturated or unsaturated, linear or branched $C_1\text{-}C_6$ hydrocarbon-based groups $R_{29}$, a hydrogen atom, $R_{24}$, $R_{26}$ and $R_{28}$, which may be identical or different, are chosen from saturated or unsaturated, linear or branched $C_7\text{-}C_{21}$ hydrocarbon-based groups;

r, s and t, which may be identical or different, are integers ranging from 2 to 6, r1 and t1, which are identical or different, have the values 0 or 1, r2+r1=2r and t1+t2=2t, y is an integer ranging from 1 to 10, x and z, which may be identical or different, are integers having values from 0 to 10, $X^-$ is a simple or complex, organic or inorganic anion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is an $R_{27}$ hydrocarbon-based group, it can be long and have from 12 to 22 carbon atoms or be short and have from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}\text{-}C_{21}$ hydrocarbon-based groups, and more particularly from linear or branched, saturated or unsaturated $C_{11}\text{-}C_{21}$ alkyl and alkenyl groups.

Preferably, x and z, which may be identical or different, have the value 0 or 1.

Advantageously, y is equal to 1.

Preferably, r, s and t, which may be identical or different, have the value 2 or 3 and more particularly still are equal to 2.

The anion $X^-$ is preferably a halide, preferably chloride, bromide or iodide, a $(C_1\text{-}C_4)$alkyl sulfate, or a $(C_1\text{-}C_4)$alkylsulfonate or $(C_1\text{-}C_4)$alkylarylsulfonate. However, use may be made of methanesulfonate, phosphate, nitrate, tosylate, an anion derived from an organic acid, such as acetate or lactate, or any other anion which is compatible with the ammonium having an ester function.

The anion $X^-$ is more particularly still chloride, methyl sulfate or ethyl sulfate.

Use is made more particularly, in the composition according to the invention, of the ammonium salts of formula (XIII) in which:

$R_{22}$ denotes a methyl or ethyl group, x and y are equal to 1, z is equal to 0 or 1, r, s and t are equal to 2, $R_{23}$ is chosen from:

the group $$R_{26} - \overset{\overset{O}{\|}}{C} -,$$

methyl, ethyl or $C_{14}\text{-}C_{22}$ hydrocarbon groups, a hydrogen atom, $R_{25}$ is chosen from:
the group

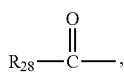

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XIII), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a majority by weight of diester salts.

It is also possible to use the ammonium salts containing at least one ester function that are described in U.S. Pat. Nos. 4,874,554 and 4,137,180.

Use may also be made of behenoylhydroxypropyltrimethylammonium chloride sold by the company Kao under the name Quartamin BTC 131, for example.

Preferably, the ammonium salts containing at least one ester function contain two ester functions.

Among the cationic surfactants, it is more particularly preferred to choose cetyltrimethylammonium, behenyltrimethylammonium and dipalmitoylethylhydroxyethyl-methylammonium salts, and mixtures thereof, and more particularly behenyl-trimethylammonium chloride, cetyltrimethylammonium chloride, and dipalmitoylethylhydroxyethylmethylammonium methosulfate, and mixtures thereof.

Preferably, the surfactant(s) is(are) chosen from cationic or non-ionic surfactants, and mixtures thereof, preferentially cationic surfactants.

The composition preferably comprises one or more surfactants in a total content ranging from 0.05% to 20% by weight, more preferentially from 0.1% to 10% by weight and better still from 0.5% to 5% by weight relative to the total weight of the composition.

Medium

The cosmetically acceptable medium that is suitable for dyeing, also known as the dye support, generally comprises water or a mixture of water and of at least one organic solvent to dissolve the compounds that are not sufficiently water-soluble.

More particularly, the organic solvents are chosen from linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

pH of the Medium

The pH of the composition according to the invention generally varies from 1 to 12. Preferably, the pH of the composition according to the invention is acidic. For the purposes of the present invention, the term "acidic" is intended to mean a pH less than 7.

Preferably, the pH of the composition according to the invention is less than 5, and particularly ranges from 1 to 4.9.

Preferably, the pH of the composition is between 2 and 4.5.

pH Adjuster

The cosmetically acceptable medium can be adjusted to the desired value by means of acidifying or basifying agents usually used in the dyeing of keratin fibres, or alternatively using standard buffer systems.

Among the acidifying agents, examples that may be mentioned include mineral acids, for instance hydrochloric or (ortho)phosphoric acid, boric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

Preferably, citric acid is used as acidifying agent.

The basifying agent(s) may be mineral, organic or hybrid.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds having formula (XII) below:

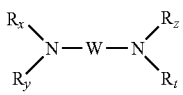

(XII)

in which W is a divalent $C_1$ to $C_6$ alkylene radical optionally substituted with one or more hydroxyl groups or a $C_1$ to $C_6$ alkyl radical, and/or optionally interrupted with one or more heteroatoms such as 0, or $NR_u$; $R_x$, $R_y$, $R_z$, $R_t$ and $R_u$, which may be identical or different, represent a hydrogen atom or a $C_1$ to $C_6$ alkyl, $C_1$ to $C_6$ hydroxyalkyl or $C_1$ to $C_6$ aminoalkyl radical.

Examples of amines of formula (IX) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the composition according to the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (XIII) below, and also salts thereof:

R—$CH_2$—$CH(NH_2)$—$C(O)$—OH (XIII)

in which R represents a group chosen from imidazolyl, preferably imidazolyl-4-yl; aminopropyl; aminoethyl; —$(CH_2)_2N(H)$—$C(O)$—$NH_2$; and —$(CH_2)_2$—$N(H)$—$C(NH)$—$NH_2$.

The compounds corresponding to formula (XIII) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines, amino acids in neutral or ionic form, in particular basic amino acids, and preferably corresponding to those having formula (XIII).

The mineral basifying agent(s) are preferably chosen from mineral alkaline agents, preferably chosen from aqueous ammonia, alkali metal carbonates or bicarbonates such as sodium or potassium carbonates and sodium or potassium bicarbonates, sodium hydroxide or potassium hydroxide or mixtures thereof, better still from sodium hydroxide or potassium hydroxide or mixtures thereof.

Additives

The composition according to the invention may in particular comprise one or more additives preferably chosen from thickening polymers, cationic polymers, fatty substances and/or additional direct dyes.

Thickening Polymers

The composition may also comprise one or more thickening polymers.

This thickening polymer is chosen from ionic or non-ionic, non-associative polymers, or from non-ionic, anionic, cationic or amphoteric, associative polymers, and also mixtures thereof.

For the purpose of the present invention, the term "thickening polymer" is intended to mean a polymer which, when introduced at 1% in a pure aqueous solution or an aqueous-alcoholic solution containing 30% ethanol, and at pH=7, makes it possible to achieve a viscosity of at least 100 cps and preferably of at least 500 cps, at 25° C. and at a shear rate of 1 $s^{-1}$. This viscosity can be measured using a cone/plate viscometer (Haake R600 rheometer or the like). Preferably, these polymers increase, through their presence, the viscosity of the compositions into which they are introduced by at least 50 cps and preferably 200 cps, at 25° C. and at a shear rate of 1 $s^{-1}$.

As regards the non-associative thickening polymers, it is first recalled that, for the purposes of the present invention, non-associative thickening polymers are thickening polymers not containing any $C_8$-$C_{30}$ fatty chains.

Among the non-associative thickening polymers present, mention may be made of:

a) crosslinked acrylic or methacrylic acid homopolymers or copolymers, b) crosslinked homopolymers of 2-acrylamido-2-methylpropanesulfonic acid, and crosslinked acrylamide copolymers thereof, c) ammonium acrylate homopolymers or copolymers of ammonium acrylate and of acrylamide, d) non-ionic guar gums, e) gums of biopolysaccharides of microbial origin, gums derived from plant exudates, f) celluloses, in particular hydroxyethyl-, hydroxypropyl- or carboxymethylcelluloses, g) pectins and alginates, h) mixtures thereof.

A first family of non-associative thickening polymers that is suitable is represented by crosslinked acrylic acid homopolymers, such as those crosslinked by an allyl ether of an alcohol from the sugar series, such as, for example, the products sold under the names Carbopol 980, 981, 954, 2984 and 5984 by the company Noveon or the products sold under the names Synthalen M and Synthalen K by the company 3 VSA.

The non-associative thickening polymers may also be crosslinked (meth)acrylic acid copolymers, such as the polymer sold under the name Aqua SF1 by the company Noveon.

The non-associative thickening polymers may be chosen from crosslinked 2-acrylamido-2-methylpropanesulfonic acid homopolymers and the crosslinked acrylamide copolymers thereof.

As regards these homopolymers and copolymers, which may be partially or totally neutralized, mention may be made of polymers comprising from 90% to 99.9% by weight, relative to the total weight of the polymer, of units of formula (j) below:

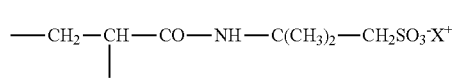

(j)

in which $X^+$ denotes a cation or a mixture of cations, or a proton.

More particularly, the cations are chosen from alkali metals (for instance sodium or potassium), ammonium ions optionally substituted with 1 to 3 alkyl radicals, which may be identical or different, containing from 1 to 6 carbon atoms, optionally bearing at least one hydroxyl radical, cations derived from N-methylglucamine or from basic amino acids, for instance arginine and lysine.

Preferably, the cation is an ammonium or sodium ion. Moreover, the polymer comprises from 0.01% to 10% by weight, relative to the total weight of the polymer, of crosslinking units derived from at least one monomer containing at least two ethylenic unsaturations (carbon-carbon double bond).

The crosslinking monomers containing at least two ethylenic unsaturations are chosen, for example, from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyloxyethanoyl, tetra- or diethylene glycol di(meth)acrylate, triallylamine, tetraallylethylenediamine, trimethylolpropane diallyl ether, trimethylolpropane triacrylate, methylenebis(meth)acrylamide or divinylbenzene, allylic ethers of alcohols of the sugar series, or other allylic or vinyl ethers of polyfunctional alcohols, and also allylic esters of phosphoric and/or vinylphosphonic acid derivatives, or mixtures of these compounds.

For further details regarding these polymers, reference may be made to document EP 815 828.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as non-associative thickening polymers, ammonium acrylate homopolymers or copolymers of ammonium acrylate and of acrylamide.

Among the ammonium acrylate homopolymers that may be mentioned by way of example is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to documents FR 2 416 723, U.S. Pat. Nos. 2,798,053 and 2,923,692 as regards the description and preparation of such compounds.

The composition may also comprise dimethylaminoethyl methacrylate homopolymers quaternized with methyl chloride or dimethylaminoethyl methacrylate copolymers quaternized with methyl chloride and acrylamide.

Among the homopolymers of this type, mention may be made of the products sold under the names Salcare SC95 and Salcare SC96 by the company Ciba. Among the copolymers of this family, mention may be made of the product Salcare SC92 sold by Ciba or the product PAS 5194 sold by Hoechst. These polymers are especially described and prepared in document EP 395 282, to which reference may be made.

By way of non-associative thickening polymers, mention may be made of non-ionic guar gums, for instance the non-modified, non-ionic guar gums sold under the name Vidogum GH 175 by the company Uni Pectin and under the name Jaguar C by the company Meyhall.

The non-ionic guar gums that may be used according to the invention are preferably modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups.

These guar gums are well known in the prior art and may be prepared, for example, by reacting the corresponding alkene oxides, for instance, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such non-ionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

By way of suitable non-associative thickening polymers, mention may also be made of biopolysaccharide gums of microbial origin, such as scleroglucan or xanthan gums.

Also suitable are gums derived from plant exudates, such as gum arabic, gum ghatti, karaya and tragacanth gums; celluloses, in particular hydroxyethyl-, hydroxypropyl- or carboxymethylcelluloses; pectines and alginates.

These polymers are well known to those skilled in the art and are in particular described in the book by Robert L. Davidson entitled "Handbook of Water soluble gums and resins" published by Mc Graw Hill Book Company (1980). It is recalled that associative polymers are hydrophilic polymers that are capable, in an aqueous medium, of reversibly associating with each other or with other molecules.

Their chemical structure more particularly comprises at least one hydrophilic region and at least one hydrophobic region.

The term "hydrophobic group" is intended to mean a radical or polymer with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferably, the hydrocarbon-based group is derived from a mono functional compound. By way of example, the hydrophobic group may be derived from a fatty alcohol such as stearyl alcohol, dodecyl alcohol or decyl alcohol. It may also denote a hydrocarbon-based polymer, such as, for example, polybutadiene.

Among the associative polymers suitable for implementing the invention, mention may be made of:

a) anionic associative polymers comprising at least one hydrophilic unit of the type of an ethylenic unsaturated anionic monomer, in particular carboxyvinylic acid, and most particularly an acrylic acid or a methacrylic acid or mixtures thereof, and at least one fatty-chain allyl ether unit comprising from 8 to 30 carbon atoms, in particular corresponding to the monomer of formula (I) below:

$$CH_2=CR'CH_2O\ B_n,\ R \qquad (I)$$

in which R' denotes H or $CH_3$, B denotes an ethylenoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10, and R denotes a stearyl radical (C18).

Anionic associative polymers of this type are described and prepared, according to an emulsion polymerization process in Patent EP-0 216 479.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide. Among the latter polymers, those most particularly preferred are crosslinked terpolymers of methacrylic acid, of ethyl acrylate and of polyethylene glycol (10 OE) stearyl alcohol ether (Steareth-10), especially those sold by the company Ciba under the names Salcare SC800 and Salcare SC900, which are aqueous 30% emulsions of a crosslinked terpolymer of methacrylic acid, of ethyl acrylate and of steareth-10 allyl ether (40/50/10);

b) anionic associative polymers comprising at least one hydrophilic unit of unsaturated olefinic carboxylic acid type, and at least one hydrophobic unit of the type such as a $(C_{10}-C_{30})$ alkyl ester of an unsaturated carboxylic acid. These polymers are preferably chosen from those for which the hydrophilic unit of unsaturated olefinic carboxylic acid type corresponds to the monomer of formula (II) below:

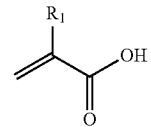

(II)

in which R1 denotes H or $CH_3$ or $C_2H_5$, i.e. acrylic acid, methacrylic acid or ethacrylic acid units, and of which the hydrophobic unit of the type such as a $(C_{10}-C_{30})$ alkyl ester of an unsaturated carboxylic acid corresponds to the monomer of formula (III) below:

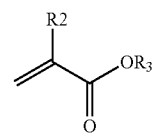

(III)

in which R2 denotes H or $CH_3$ or $C_2H_5$ (i.e. acrylate, methacrylate or ethacrylate units) and preferably H (acrylate units) or $CH_3$ (methacrylate units), R3 denoting a $C_{10}-C_{30}$ and preferably $C_{12}-C_{22}$ alkyl radical.

$(C_{10}-C_{30})$ alkyl esters of unsaturated carboxylic acids in accordance with the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Use will more particularly be made, among anionic associative polymers of this type, of polymers formed from a mixture of monomers comprising:
essentially acrylic acid,
an ester of formula (III) described above and in which R2 denotes H or $CH_3$, R3 denoting an alkyl radical containing from 12 to 22 carbon atoms, and
a crosslinking agent, which is a well-known copolymerizable unsaturated polyethylenic monomer, for instance diallyl phthalate, allyl (meth)acrylate, divinylbenzene, (poly)ethylene glycol dimethacrylate and methylenebisacrylamide.

Among the anionic associative polymers of this type, use will be made more particularly of those formed from 95% to 60% by weight of acrylic acid (hydrophilic unit), 4% to 40% by weight of $C_{10}-C_{30}$ alkyl acrylate (hydrophobic unit) and 0 to 6% by weight of crosslinking polymerizable monomer, or alternatively those formed from 98% to 96% by weight of acrylic acid (hydrophilic unit), 1% to 4% by weight of $C_{10}-C_{30}$ alkyl acrylate (hydrophobic unit) and 0.1% to 0.6% by weight of crosslinking polymerizable monomer such as those described previously.

Among said polymers above, preference is very particularly given, according to the present invention, to the products sold by the company Goodrich under the trade names Pemulen TR1®, Pemulen TR2® and Carbopol 1382®, and even more preferentially Pemulen TR1®, and to the product sold by the company SEPPIC under the name Coatex SX®.

Mention may also be made of polymers which, besides the monomers of formula (II) and of formula (III), contain one or more other monomers. This additional monomer may especially be a vinyllactam and in particular vinylpyrrolidone.

An example of a polymer that may be mentioned is the acrylic acid/lauryl methacrylate/vinylpyrrolidone terpolymer sold under the name Acrylidone LM by the company ISP;

(c) maleic anhydride/$C_{30}$-$C_{38}$ alpha-olefin/alkyl maleate anionic associative terpolymers, such as the product (maleic anhydride/$C_{30}$-$C_{38}$ alpha-olefin/isopropyl maleate copolymer) sold under the name Performa V 1608® by the company Newphase Technologies;

d) acrylic anionic associative terpolymers comprising:
(i) 20% to 70% by weight of an α,βmonoethylenically unsaturated carboxylic acid,
(ii) 20% to 80% by weight of a non-surfactant, α,βmonoethylenically unsaturated monomer other than (i),
(iii) 0.5% to 60% by weight of a non-ionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 OE) terpolymer, as an aqueous 25% dispersion;

e) anionic associative copolymers comprising, among their monomers, a carboxylic acid having α,βmonoethylenic unsaturation and an ester of carboxylic acid having α,βmonoethylenic unsaturation and of an oxyalkylenated fatty alcohol.

Preferentially, these compounds also comprise as monomer an ester of an α,βmonoethylenically unsaturated carboxylic acid and of a $C_1$-$C_4$ alcohol.

By way of example of this type of compound, mention may be made of Aculyn® 22 sold by the company Rohm and Haas, which is an oxyalkylenated methacrylic acid/ethyl acrylate/stearyl methacrylate terpolymer;

f) associative celluloses modified with groups comprising at least 30 one fatty chain, such as alkyl, arylalkyl or alkylaryl groups comprising from 8 to 30 carbon atoms;

g) quaternized hydroxyethylcelluloses modified with groups comprising at least one fatty chain, such as alkyl, arylalkyl or alkylaryl groups comprising from 8 to 30 carbon atoms.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200®, Quatrisoft LM-X529-18-A®, Quatrisoft LM-X529-18B® ($C_{12}$ alkyl) and Quatrisoft LM-X529-8® ($C_{18}$ alkyl) sold by the company Amerchol and the products Crodacel QM®, Crodacel QL® ($C_{12}$ alkyl) and Crodacel QS® ($C_{18}$ alkyl) sold by the company Croda;

(h) the cationic polymer(s) obtained by polymerization of a monomer mixture comprising one or more vinyl monomers substituted with one or more amino groups, one or more hydrophobic non-ionic vinyl monomers, and one or more associative vinyl monomers.

In particular, among these cationic polymers, mention may be made especially of the compound sold by the company Noveon under the name Aqua CC and which corresponds to the INCI name Polyacrylate-1 Crosspolymer. Polyacrylate-1 Crosspolymer is the product of polymerization of a monomer mixture comprising:

a di($C_1$-$C_4$ alkyl)amino($C_1$-$C_6$ alkyl) methacrylate,
one or more $C_1$-$C_{30}$ alkyl esters of (meth)acrylic acid,
a polyethoxylated $C_{10}$-$C_{30}$ alkyl methacrylate (20-25 mol of ethylene oxide units),
a 30/5 polyethylene glycol/polypropylene glycol allyl ether,
a hydroxy($C_2$-$C_8$ alkyl) methacrylate, and
an ethylene glycol dimethacrylate;

i) the amphoteric associative polymers prepared by copolymerizing:
1) at least one monomer of formula (Ibis) or (IIbis) below:

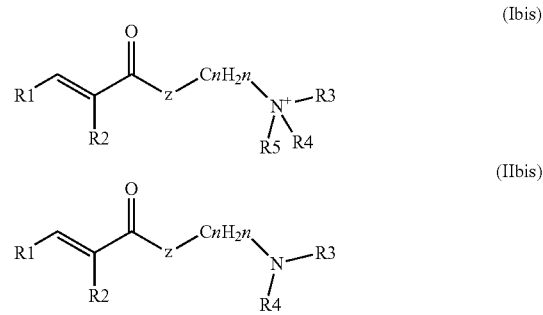

in which R1 and R2, which may be identical or different, represent a hydrogen atom or a methyl radical, R3, R4 and R5, which may be identical or different, represent a linear or branched alkyl radical containing from 1 to 30 carbon atoms, Z represents an NH group or an oxygen atom,
n is an integer from 2 to 5,
$A^-$ is an anion derived from an organic or mineral acid, such as a methosulfate anion or a halide such as chloride or bromide;
2) at least one monomer of formula (IIIbis):

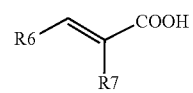

in which R6 and R7, which may be identical or different, represent a hydrogen atom or a methyl radical; and
3) at least one monomer of formula (IVbis):

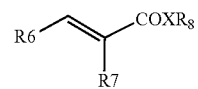

in which R6 and R7, which may be identical or different, represent a hydrogen atom or a methyl radical, X denotes an oxygen or nitrogen atom and R8 denotes a linear or branched alkyl radical containing from 1 to 30 carbon atoms; at least one of the monomers of formula (Ibis), (IIbis) or (IIIbis) comprising at least one fatty chain comprising 8 to 30 carbon atoms.

The monomers of formulae (Ibis) and (IIbis) of the present invention are preferably chosen from the group constituted of:
dimethylaminoethyl methacrylate, dimethylaminoethyl acrylate,
diethylaminoethyl methacrylate, diethylaminoethyl acrylate, dimethylaminopropyl methacrylate, dimethylaminopropyl acrylate,
dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

More particularly, the monomer of formula (Ibis) is chosen from acrylamidopropyltrimethylammonium chloride and methacrylamidopropyltrimethylammonium chloride.

The monomers of formula (IIIbis) of the present invention are preferably chosen from the group constituted of acrylic acid, methacrylic acid, crotonic acid and 2-methylcrotonic acid. More particularly, the monomer of formula (VII) is acrylic acid.

The monomers of formula (IV) of the present invention are preferably chosen from the group constituted of $C_{12}$-$C_{22}$ and more particularly $C_{16}$-$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Ibis), (IIbis) or (IVbis)), and preferably from 1.5 mol % to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers such as non-ionic monomers and in particular such as $C_1$-$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers;

j) non-ionic associative celluloses modified with groups comprising at least one fatty chain comprising from 8 to 30 carbon atoms and preferably from 10 to 22 carbon atoms, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyl) sold by the company Aqualon, or the product Bermocoll EHM 100® sold by the company Berol Nobel.

Also suitable are those modified with alkylphenyl polyalkylene glycol ether groups, such as the product Amercell Polymer HM-1500® (nonylphenyl polyethylene glycol (15) ether) sold by the company Amerchol;

k) associative non-ionic hydroxypropyl guars modified with groups comprising at least one fatty chain comprising from 8 to 30 carbon atoms and preferably from 10 to 22 carbon atoms, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhodia;

l) associative non-ionic copolymers of vinylpyrrolidone and of hydrophobic monomers comprising a fatty chain comprising from 8 to 30 carbon atoms and preferably from 10 to 22 carbon atoms, of which mention may, by way of example, be made of:

the products Antaron V216® or Ganex V216® (vinylpyrrolidone/hexadecene copolymer), sold by the company ISP,
the products Antaron V220® or Ganex V220® (vinylpyrrolidone/eicosene copolymer), sold by the company ISP;

m) associative non-ionic copolymers of $C_1$-$C_6$ alkyl methacrylates or acrylates and of amphiphilic monomers comprising at least one fatty chain comprising from 8 to 30 carbon atoms and preferably from 10 to 22 carbon atoms, which are preferably oxyethylenated, for instance the oxyethylenated methyl acrylate/stearyl acrylate copolymer sold by the company Goldschmidt under the name Antil 208®;

n) associative non-ionic copolymers of hydrophilic methacrylates or acrylates and of hydrophobic monomers comprising at least one fatty chain comprising from 8 to 30 carbon atoms and preferably from 10 to 22 carbon atoms, for instance the polyethylene glycol methacrylate/lauryl methacrylate copolymer;

o) associative non-ionic polyether polyurethanes comprising, in their chain, both hydrophilic blocks, which are preferably polyoxyethylenated, and hydrophobic blocks which may be aliphatic sequences alone and/or cycloaliphatic and/or aromatic sequences comprising from 8 to 30 carbon atoms and preferably from 10 to 22 carbon atoms;

p) associative non-ionic polymers with an aminoplast ether backbone having at least one fatty chain comprising from 8 to 30 carbon atoms and preferably from 10 to 22 carbon atoms, such as the compounds Pure Thix® provided by the company Sud-Chemie;

q) mixtures thereof.

Preferably, the thickening polymer(s) are chosen from celluloses, in particular hydroxyethyl-, hydroxypropyl- or carboxymethylcelluloses.

Advantageously, the content of thickening polymer ranges from 0.01% to 10% by weight, preferably from 0.1% to 5% by weight and better still from 0.2% to 3% by weight relative to the total weight of the composition. Alkaline agent:

Cationic Polymer

The cosmetic composition may also comprise one or more cationic polymers.

For the purposes of the present invention, the term "cationic polymer" denotes any polymer containing cationic groups and/or groups that can be ionized into cationic groups.

The cationic polymers that may be present in the composition according to the invention may be chosen from any of those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or be carried by a side substituent directly attached thereto.

The cationic polymers used generally have a number-average molecular mass of between 500 and $5\times10^6$ approximately and preferably between $10^3$ and $3\times10^6$ approximately.

Among the cationic polymers, mention may more particularly be made of polymers of the polyamine, polyaminoamide and polyquaternary ammonium type.

These are known products. They are especially described in French patents 2 505 348 and 2 542 997. Among said polymers, mention may be made of:

(1) homopolymers or copolymers derived from acrylic or methacrylic esters or amides and comprising at least one of the units of formula (IX), (X), (XI) or (XII) below:

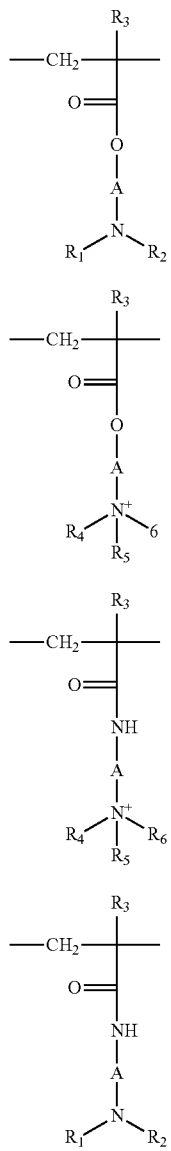

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

X denotes an anion derived from a mineral or organic acid, such as a methosulfate anion or a halide such as chloride or bromide.

Mention may be made in particular of the ethyltrimethylammonium methacrylate chloride homopolymer.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, the crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba;

(2) the cellulose ether derivatives containing quaternary ammonium groups, described in French patent 1 492 597, and in particular the polymers sold under the names Ucare Polymer "JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group;

(3) cellulose copolymers or cellulose derivatives grafted with a water-soluble quaternary ammonium monomer, and described especially in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch;

(4) the cationic guar gums described more particularly in U.S. Pat. No. 3,589,578 and 4 031 307, such as guar gums containing cationic trialkylammonium groups. Guar gums modified with a 2,3-epoxypropyltrimethylammonium salt (e.g. chloride) are used, for example.

Such products are sold in particular under the trade names Jaguar C13 S, Jaguar C 15, Jaguar C 17 or Jaguar C162 by the company Rhodia;

(5) polymers constituted of piperazinyl units and of divalent alkylene or hydroxyalkylene radicals containing straight or branched chains, optionally interrupted with oxygen, sulfur or nitrogen atoms or by aromatic or heterocyclic rings, and also the oxidation and/or quaternization products of these polymers. Such polymers are described, in particular, in French patents 2 162 025 and 2 280 361;

(6) water-soluble polyaminoamides prepared in particular by polycondensation of an acid compound with a polyamine; these polyaminoamides can be crosslinked by an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively by an oligomer resulting from the reaction of a difunctional compound which is reactive with regard to a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they contain one or more tertiary amine functional groups, quaternized. Such polymers are especially described in French patents 2 252 840 and 2 368 508;

(7) polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are in particular described in French patent 1 583 363.

Among these derivatives, mention may be made more particularly of the adipic acid/dimethylamino-hydroxy-propyl/diethylenetriamine polymers sold under the name Cartaretine F, F4 or F8 by the company Sandoz;

(8) polymers obtained by reaction of a polyalkylene polyamine containing two primary amine groups and at least one secondary amine group with a dicarboxylic acid chosen from diglycolic acid and saturated aliphatic dicarboxylic acids containing from 3 to 8 carbon atoms. The mole ratio between the polyalkylene polyamine and the dicarboxylic acid is between 0.8:1 and 1.4:1; the polyaminoamide resulting therefrom is reacted with epichlorohydrin in a mole ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are sold in particular under the name Hercosett 57 by Hercules Inc. or else under the name PD 170 or Delsette 101 by Hercules in the case of the adipic acid/epoxypropyl/diethylenetriamine copolymer;

(9) cyclopolymers of alkyldiallylamine or of dialkyldiallylammonium, such as homopolymers or copolymers comprising, as main constituent of the chain, units corresponding to formula (XIII) or (XIV):

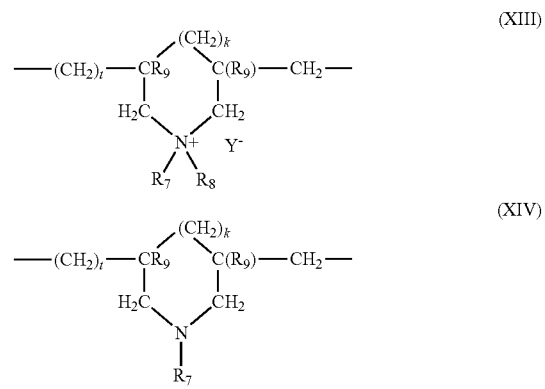

in which formulae k and t are equal to 0 or 1, the sum k+t being equal to 1; $R_9$ denotes a hydrogen atom or a methyl radical; $R_7$ and $R_8$, independently of each other, denote an alkyl group containing from 1 to 6 carbon atoms, a hydroxyalkyl group in which the alkyl group preferably contains 1 to 5 carbon atoms, or a lower ($C_1$-$C_4$) amidoalkyl group, or $R_7$ and $R_8$ may denote, together with the nitrogen atom to which they are attached, heterocyclic groups, such as piperidyl or morpholinyl; $R_7$ and $R_8$, independently of each other, preferably denote an alkyl group containing from 1 to 4 carbon atoms; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

Among the polymers defined above, mention may be made more particularly of the dimethyldiallylammonium chloride homopolymer sold under the name Merquat 100 by the company Nalco (and its homologues of low weight-average molecular mass) and the copolymers of diallyldimethylammonium chloride and of acrylamide, sold under the names Merquat 550 and Merquat 7SPR;

(10) quaternary diammonium polymer containing repeating units corresponding to formula (XV):

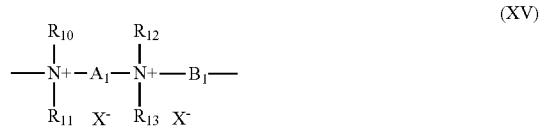

in which formula (XV):

$R_{10}$, $R_{11}$, $R_{12}$ and $R_{13}$, which may be identical or different, represent aliphatic, alicyclic or arylaliphatic radicals containing from 1 to 6 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

A1 and B1 represent polymethylene groups containing from 2 to 8 carbon atoms, which may be linear or branched and saturated or unsaturated and may contain, bonded to or intercalated in the main chain, one or more aromatic rings, or one or more oxygen or sulfur atoms, or sulfoxide, sulfone, disulfide, amino, alkylamino, hydroxyl, quaternary ammonium, ureido, amide or ester groups, and $X^-$ denotes an anion derived from a mineral or organic acid;

A1, $R_{10}$ and $R_{12}$ can form, with the two nitrogen atoms to which they are attached, a piperazine ring; in addition, if A1 denotes a linear or branched, saturated or unsaturated alkylene or hydroxyalkylene radical, B1 can also denote a group —($CH_2$)n-CO-D-OC—($CH_2$)n- in which D denotes:

a) a glycol residue of formula: —O—Z—O—, where Z denotes a linear or branched hydrocarbon-based radical or a group corresponding to one of the following formulae:

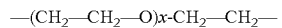

—($CH_2$—$CH_2$—O)x-$CH_2$—$CH_2$—

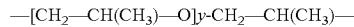

—[$CH_2$—CH($CH_3$)—O]y-$CH_2$—CH($CH_3$)— where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical

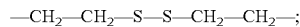

—$CH_2$—$CH_2$—S—S—$CH_2$—$CH_2$—;

d) a ureylene group of formula: —NH—CO—NH—.

Preferably, $X^-$ is an anion, such as chloride or bromide.

These polymers have a number-average molecular weight generally between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that are formed from repeating units corresponding to formula (XVI) below:

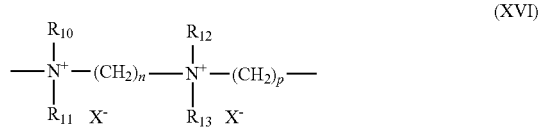

(XVI)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 8 approximately, and $X^-$ is an anion derived from a mineral or organic acid. Mention may be made in particular of Mexomer PO sold by the company Chimex;

(11) Polyquaternary ammoniums formed from repeating units of formula (XVII):

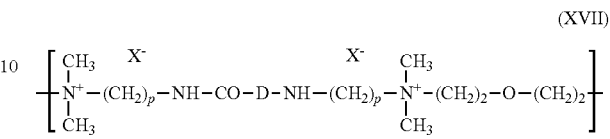

(XVII)

in which p denotes an integer ranging from 1 to 6 approximately, D may be nothing or may represent a group —($CH_2$)$_r$—CO— in which r denotes a number equal to 4 or 7, and $X^-$ is an anion.

Such polymers may be prepared according to the processes described in U.S. Pat. Nos. 4,157,388, 4,702,906 and 4,719,282. They are especially described in patent application EP-A-122 324.

Among these polymers, examples that may be mentioned include the products Mirapol A 15, Mirapol AD1, Mirapol AZ1 and Mirapol 175 sold by the company Miranol;

(12) quaternary polymers of vinylpyrrolidone and of vinylimidazole, for instance the products sold under the names Luviquat FC 905, FC 550 and FC 370 by the company BASF. These polymers may also comprise other monomers, for instance diallyldialkylammonium halides. Mention may be made in particular of the product sold under the name Luviquat Sensation by the company BASF;

(13) polyamines such as Polyquart H sold by Henkel, which is given under the reference name Polyethylene glycol (15) Tallow Polyamine in the CTFA dictionary, or oxyethylenated (15 OE) coconut polyamines.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, it is preferred to use polymers of families (1), (2), (3), (4), (9), (10) and (12).

Preferably, the cationic polymer(s) are chosen from cationic celluloses, cationic guar gums and dimethyldiallylammonium halide homopolymers or copolymers.

More preferentially, the cationic polymer(s) are chosen from hydroxyalkylcelluloses, such as hydroxymethyl-, hydroxyethyl- or hydroxypropylcelluloses grafted especially with a methacryloyl-ethyltrimethylammonium, methacrylamidopropyl-trimethylammonium or dimethyldiallylammonium salt, cationic guar gums, and dimethyldiallylammonium chloride homopolymers or copolymers.

The content of cationic polymer(s) in the composition according to the invention may range from 0.05% to 5% by weight relative to the total weight of the composition, preferably from 0.1% to 3% by weight and more preferentially from 0.2% to 1.5% by weight relative to the total weight of the composition.

Fatty Substances

Preferably, the composition according to the invention may comprise one or more fatty substances.

For the purposes of the present invention, the term "fatty substance" is intended to mean an organic compound that is insoluble in water at ordinary ambient temperature (20-25° C.) and at atmospheric pressure (760 mmHg, i.e. $1.013 \times 10^5$ Pa), with a solubility in water of less than 5%, preferably less than 1% and even more preferentially less than 0.1%. The fatty substances generally have in their structure a hydrocarbon-based chain comprising at least 6 carbon atoms. In addition, the fatty substances are generally soluble in organic solvents under the same temperature and pressure conditions, for instance chloroform, ethanol, benzene, liquid petroleum jelly or decamethylcyclopentasiloxane.

The fatty substances are, moreover, non-(poly)oxyalkylenated and non-(poly)glycerolated. In other words, the fatty substances do not comprise in their structure a (poly) ethylene oxide or (poly)glycerol or (poly)propylene glycol unit.

Preferably, the composition according to the invention comprises a total content of fatty substances of greater than or equal to 3% by weight relative to the total weight of the composition.

Preferably, the fatty substance(s) are present in the composition according to the invention in a total content ranging from 0.1% to 20% by weight, preferably from 1% to 15% by weight and more preferentially from 3% to 10% by weight relative to the total weight of the composition.

The fatty substance(s) may be chosen from solid fatty substances and/or liquid fatty substances (also called "oil"), and mixtures thereof.

The term "oil" is intended to mean a "fatty substance" that is liquid, i.e. that is capable of flowing under the action of its own weight at ambient temperature (25° C.) and at atmospheric pressure (760 mmHg, i.e. $1.013 \times 10^5$ Pa). Preferably, the viscosity at a temperature of 25° C. and at a shear rate of $1\ s^{-1}$ of the oil is between $10^{-3}$ Pa·s and 2 Pa·s. It may be measured using a Thermo Haake RS600 rheometer with cone-plate geometry or an equivalent machine.

For the purposes of the present invention, the term "solid fatty substance" is intended to mean a fatty substance that is not liquid at ambient temperature (20-25° C.) and atmospheric pressure (760 mmHg, i.e. $1.013 \times 10^5$ Pa), in particular a solid compound or a compound having a viscosity of greater than 2 Pa·s at a shear rate of $1\ s^{-1}$ under the conditions mentioned above.

The solid fatty substances used in the composition according to the invention have a melting point greater than ambient temperature, preferably a melting point greater than or equal to 40° C., preferentially ranging from 46 to 95° C.

In particular, the fatty substance may be chosen from hydrocarbon-based fatty substances, silicone-based fatty substances other than the amino silicones previously described, and/or fluorinated fatty substances.

The term "hydrocarbon-based fatty substance" is intended to mean a fatty substance formed essentially of, or even constituted of, carbon and hydrogen atoms, and optionally of oxygen or nitrogen atoms, and not comprising any silicon or fluorine atoms. It may contain alcohol, ester, ether, carboxylic acid, amine and/or amide groups.

The hydrocarbon-based fatty substance may in particular be chosen from hydrocarbons, fatty substances of animal origin, fatty substances of plant origin, fatty alcohols, fatty esters and fatty ethers.

According to a first embodiment, the fatty substance may be a silicone-based fatty substance.

The term "silicone-based fatty substance" is intended to mean a fatty substance containing at least one silicon atom. The term "non-silicone fatty substance" is intended to mean a fatty substance not containing any silicon (Si) atoms.

According to one embodiment, the silicone-based fatty substance other than amino silicones may be a liquid silicone oil (aka silicone oil or liquid silicone). The term "liquid silicone" is intended to mean an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, in particular liquid polydimethylsiloxanes (PDMSs), and liquid polyorganosiloxanes comprising at least one aryl group.

The polydialkylsiloxanes are in particular chosen from polydimethylsiloxanes comprising trimethylsilyl end groups, and polydimethylsiloxanes comprising dimethylsilanol end groups, known under the name dimethiconol (CTFA). The polyorganosiloxanes comprising aryl groups are in particular chosen from polydiarylsiloxanes, in particular polydiphenylsiloxanes, and polyalkylarylsiloxanes.

According to a second embodiment, the fatty substance may be fluorinated. The term "fluorinated fatty substance" is intended to mean a fatty substance containing at least one fluorine atom.

In particular, by way of fluorinated fatty substance, mention may be made of fluorinated oils such as perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

According to a preferred third embodiment, the fatty substance is a hydrocarbon-based fatty substance as defined above. In particular, preferably, the hydrocarbon-based fatty substance(s) are chosen from hydrocarbon-based oils and hydrocarbon-based solid fatty substances, and mixtures thereof. Preferably, the hydrocarbon-based fatty substance (s) are advantageously chosen from hydrocarbons containing more than 16 carbon atoms, $C_6$-$C_{16}$ alkanes, triglycerides or oils of plant origin, liquid synthetic triglycerides, fatty alcohols, esters of fatty acids and/or of fatty alcohols other than triglycerides and non-silicone waxes, or mixtures thereof.

According to a first variant of the invention, the hydrocarbon-based fatty substance is an oil.

Preferably, the hydrocarbon-based oils are chosen from:
halogenated or non-halogenated linear or branched hydrocarbons, of mineral or synthetic origin, containing less than 16 carbon atoms, for instance hexane, cyclohexane, undecane, dodecane, isododecane or tridecane, or more than 16 carbon atoms, such as liquid petroleum jelly, liquid paraffin, polydecenes of formula C10nH[(20n)+2] in which n ranges from 3 to 9 and preferably from 3 to 7, and mixtures thereof;

unsaturated or branched liquid fatty alcohols comprising from 6 to 30 carbon atoms, such as those of formula CnH2n+1OH with n an integer between 6 and 20 inclusive. Mention may be made especially of oleyl alcohol, linolenyl alcohol, linoleyl alcohol, ricinoleyl alcohol, undecylenyl alcohol, isostearyl alcohol and octyldodecanol;

triglyceride oils of plant or synthetic origin, such as liquid fatty acid triglycerides comprising from 6 to 30 carbon atoms, for instance heptanoic or octanoic acid triglycerides, or alternatively, for example, sunflower oil, maize oil, soy bean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil; and liquid esters other than triglycerides.

These esters are preferably liquid esters of saturated or unsaturated, linear or branched, $C_1$-$C_{26}$ aliphatic monoacids or polyacids and of saturated or unsaturated, linear or branched, $C_1$-$C_{26}$ aliphatic monoalcohols or polyalcohols, the total number of carbon atoms in the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of mono-, di- or tricarboxylic acids and of $C_4$-$C_{26}$ non-sugar di-, tri-, tetra- or pentahydroxylated alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

The composition may further comprise, as liquid fatty ester, sugar esters and diesters of $C_6$-$C_{30}$ fatty acids, preferably $C_{12}$-$C_{22}$ fatty acids. It is recalled that the term "sugar" is intended to mean oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

The hydrocarbon-based oils are preferably chosen from the polydecenes of formula C10nH[(20n)+2] in which n ranges from 3 to 9 and preferably from 3 to 7, fatty alcohols, esters and in particular esters of fatty alcohols or of fatty acids, sugar esters or diesters of $C_{12}$-$C_{24}$ fatty acids, cyclic esters, cyclic ethers, mineral oils, plant oils or animal oils, or mixtures thereof.

Preferably, the liquid fatty substance(s) are chosen from the polydecenes of formula C10nH[(20n)+2] in which n ranges from 3 to 9 and preferably from 3 to 7, fatty alcohols, such as octyldodecanol or isostearyl alcohol, esters of fatty alcohols or of fatty acids, liquid petroleum jelly and liquid paraffin, and mixtures thereof.

When the composition according to the invention comprises one or more liquid fatty substances, the fatty substance(s) that are liquid at ambient temperature are preferably present in the composition according to the invention in a total content ranging from 0.1% to 20% by weight, preferably from 1% to 15% by weight and more preferentially from 3% to 10% by weight relative to the total weight of the composition.

According to a second preferred variant of the invention, the composition according to the invention comprises at least one solid fatty substance, which is preferably hydrocarbon-based. The composition according to the invention thus comprises one or more solid, hydrocarbon-based fatty substances.

Preferably, the solid fatty substance(s) are chosen from fatty alcohols, and esters of fatty acids and/or of fatty alcohols, and/or waxes, and also mixtures thereof.

According to one preferred embodiment, the solid fatty substance(s) are hydrocarbon-based fatty substances, preferably chosen from solid fatty alcohols and/or solid esters of fatty acids and/or fatty alcohols. Preferably, the solid hydrocarbon-based fatty substances are chosen from linear or branched, saturated or unsaturated solid fatty alcohols comprising from 14 to 30 carbon atoms and/or solid esters derived from $C_9$-$C_{26}$ fatty acids and from $C_9$-$C_{26}$ fatty alcohols. Preferably, the solid fatty alcohols are saturated or unsaturated, and linear or branched, and comprise from 14 to 30 carbon atoms. Preferably, the fatty alcohol(s) are chosen from saturated and linear fatty alcohols comprising from 14 to 30 and preferably from 16 to 22 carbon atoms.

In addition, it is understood that the fatty alcohols do not comprise $C_2$-$C_3$ oxyalkylenated unit(s) or glycerolated unit(s).

Preferably, the solid fatty substance(s) are chosen from cetyl alcohol, stearyl alcohol, behenyl alcohol and a mixture thereof. Cetylstearyl alcohol may for example be used.

The hydrocarbon-based solid fatty substance(s) can also be chosen from solid esters of fatty acids and/or of fatty alcohols; mention may in particular be made of the solid esters derived from $C_9$-$C_{26}$ fatty acids and from $C_9$-$C_{26}$ fatty alcohols.

In particular, these esters may be chosen from octyldodecyl behenate, isocetyl behenate, cetyl lactate, stearyl octanoate, octyl octanoate, cetyl octanoate, decyl oleate, myristyl stearate, octyl palmitate, cetyl palmitate, octyl pelargonate, octyl stearate, alkyl myristates such as cetyl myristate, myristyl myristate or stearyl myristate, and hexyl stearate.

Preferably, the fatty substance(s) that are solid at ambient temperature are present in the composition according to the invention in a total content ranging from 0.1% to 20% by weight, preferably from 1% to 15% by weight and more preferentially from 3% to 10% by weight relative to the total weight of the composition.

Preferably, the composition according to the invention comprises one or more non-silicone, more particularly solid, fatty substances.

Additional Direct Dyes

The composition according to the invention may optionally comprise at least one additional direct dye conventionally used for the dyeing of keratin fibres. It may be chosen from cationic and non-ionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanin dyes, and natural dyes, alone or as mixtures.

It may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(βaminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine and 1-amino-2-nitro-4-hydroxy-5-methylbenzene.

The additional direct dye may also be chosen from yellow and green-yellow nitrobenzene direct dyes. Examples that may be mentioned include the compounds chosen from: 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-di(βhydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(βureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Mention may also be made of blue or violet nitrobenzene direct dyes, for instance 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(βhydroxyethyl)amino-4-(N-methyl-N-β-hydroxyethyl)amino-2-nitrobenzene, 1-(βhydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, and the 2-nitro-para-phenylenediamines of formula (III) below:

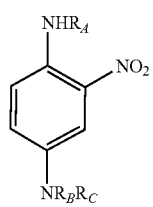

(III)

in which:

$R_B$ represents a $C_1$-$C_4$ alkyl radical or a β-hydroxyethyl, β-hydroxypropyl or γ-hydroxypropyl radical;

$R_A$ and $R_C$, which may be identical or different, represent a β-hydroxyethyl, β-hydroxypropyl, γ-hydroxypropyl or β,γ-dihydroxypropyl radical, at least one of the radicals $R_B$, $R_C$ or $R_A$ representing a γ-hydroxypropyl radical and $R_B$ and $R_C$ not being able simultaneously to denote a β-hydroxyethyl radical when $R_B$ is a γ-hydroxypropyl radical, such as those described in French patent FR 2 692 572.

Among the azo direct dyes that may be used according to the invention, mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these compounds, mention may be made most particularly of the following dyes: 1,3-dimethyl-2-[[4-(dimethylamino)phenyl]azo]-1H-imidazolium halides, 1,3-dimethyl-2-[(4-aminophenyl)azo]-1H-imidazolium halides, 1-methyl-4-[(methylphenylhydrazono)methyl]-pyridinium halides or alkyl sulfates.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(βhydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylamino anthraquinone, 1-aminopropylamino anthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes, mention may be made of the following compounds: Basic Blue 17, Basic Red 2.

Among the indoamine dyes that may be used according to the invention, mention may be made of the following compounds: 2β-hydroxyethylamino-5-[bis(β-4'-hydroxyethyl)amino]anilino-1,4-benzoquinone, 2β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N(3'-chloro-4'-methylamino)phenylureido-6-methyl-1,4-benzoquinoneimine and 3-[4'-N-(ethylcarbamylmethyl)amino]phenylureido-6-methyl-1,4-benzoquinoneimine.

Among the dyes of tetraazapentamethine type that may be used according to the invention, mention may be made of the following compounds: 2-((E)-{(E)-[(1,3-dimethyl-1,3-dihydro-2H-imidazol-2-ylidene)hydrazono]methyl}diazenyl)-1,3-dimethyl-1H-imidazol-3-ium chloride; 2-{(E)-[(1Z)—N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2(1H)-ylidene)hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)pyridinium chloride; 1-(2-hydroxyethyl)-2-[(E)-((1E)-1-{(2E)-[1-(2-hydroxyethyl)pyridin-2(1H)-ylidene]hydrazono}ethyl)diazenyl] pyridinium chloride; 1-methyl-2-((E)-{(E)-[(2Z)-(1-methylpyridin-2(1H)-ylidene)hydrazono]methyl}diazenyl)

pyridinium chloride; 1-(2-hydroxyethyl)-2-[(E)-((E)-{(2E)-[1-(2-hydroxyethyl)pyridin-2(1H)-ylidene]hydrazono}methyl)diazenyl]pyridinium acetate.

Among the additional natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and in particular henna-based poultices or extracts.

When they are present, the content of additional direct dyes in the composition generally ranges from 0.001% to 20% and preferably from 0.01% to 10% by weight relative to the weight of the composition.

Other Additives:

The composition according to the invention may also contain various adjuvants conventionally used in hair dyeing compositions, such as anionic, non-ionic, amphoteric or zwitterionic polymers or mixtures thereof; mineral thickeners, and in particular fillers such as clays or talc; antioxidants; penetrants; sequestrants; fragrances; dispersants; film-forming agents; ceramides; preservatives; opacifiers.

The above adjuvants are generally present in an amount for each of them of between 0.01% and 20% by weight relative to the weight of the composition or by weight of the ready-to-use composition.

Needless to say, those skilled in the art will take care to select this or these optional additional compound(s) such that the advantageous properties intrinsically associated with the dyeing composition that is useful in the context of the invention are not, or are not substantially, adversely affected by the envisaged addition(s).

The dyeing composition that is useful in the context of the invention may be in various forms, such as in the form of liquids, creams or gels, or in any other form that is suitable for dyeing keratin fibres, and especially human hair.

Process

The process for dyeing keratin fibres, in particular human keratin fibres such as the hair, consists in applying to said fibres the composition according to the invention.

In particular, the dyeing composition used in the process according to the invention is applied to wet or dry keratin fibres.

It is usually left in place on the fibres for a time generally of from 1 minute to 1 hour and preferably from 5 minutes to 30 minutes.

The temperature during the dyeing process conventionally ranges from ambient temperature (between 15° C. and 25° C.) to 80° C., preferably from ambient temperature to 60° C.

After the treatment, the human keratin fibres are advantageously rinsed with water. They may optionally be washed with a shampoo, followed by rinsing with water, before being dried or left to dry.

Use

The present invention also relates to the use of the dyeing composition as defined previously for dyeing keratin fibres, in particular human keratin fibres such as the hair.

The examples that follow serve to illustrate the invention without, however, being limiting in nature.

EXAMPLES

In the examples that follow, the colour build-up ($\Delta E_{ab}^*$) was evaluated in the CIE L*a*b* system.

In this L*a*b* system, L* represents the intensity of the colour, a* indicates the green/red colour axis and b* the blue/yellow colour axis. The lower the value of L*, the darker or more intense the colour.

The value of $\Delta E_{ab}^*$ was calculated from the values of L*a*b* according to equation (i) below:

$$\Delta E_{ab}^* = \sqrt{(L^*-L_o^*)^2+(a^*-a_o^*)^2+(b^*-b_o^*)^2} \tag{i}$$

The colour build-up ($\Delta E_{Lab}^*$) was calculated from the colorimetric values for locks of untreated hair ($L_o^*$, $a_o^*$ and $b_o^*$) and locks of dyed hair (L*, a* and b*).

The greater the value of $\Delta E_{ab}^*$, the better the colour build-up for the treated fibres.

In the examples that follow, all the amounts are given as weight percentages of active materials relative to the total weight of the composition, unless otherwise indicated.

I. Example 1 a. Compositions Tested

Compositions (A1) and (B1) below were prepared from the ingredients as described below, the contents of which are indicated in gram % (unless otherwise mentioned) in Table 1 below.

TABLE 1

| Chemical name | Composition A1 according to the invention Invention (g %) | Composition B1 according to the invention Invention (g %) |
| --- | --- | --- |
| Sodium hydroxide | pH = 3.5 | pH = 3.5 |
| Citric acid | 0.025 | 0.025 |
| HC Blue No. 15 | 0.2 | — |
| Basic Violet 2 | — | 0.1 |
| Cetylstearyl Alcohol (50/50 C16/C18) | 3.75 | 3.75 |
| Cetyl Alcohol | 1 | 1 |
| Hydroxyethylcellulose (MW: 1 300 000) | 0.2 | 0.2 |
| Hydroxypropyl guar trimethylammonium chloride | 0.1 | 0.1 |
| Polydimethylsiloxane containing amino ethyl aminopropyl groups, containing methoxy and/or hydroxyl and alpha-omega silanol functions, as a cationic 60% aqueous emulsion (1) | 2 | 2 |

TABLE 1-continued

| Chemical name | Composition A1 according to the invention Invention (g %) | Composition B1 according to the invention Invention (g %) |
|---|---|---|
| Deionized water | qs 100 | qs 100 |
| Preservatives | qs | qs |
| Behenyltrimethylammonium chloride as an aqueous solution containing 79% am | 2.6 | 2.6 |

(1) Amodimethicone (and) Trideceth-6 (and) cetrimonium chloride sold under the reference Xiameter MEM-8299 Emulsion by Dow Coming Compositions (A1) and (B1) are compositions according to the invention.

b. Direct Dyes Tested

The direct dyes used in compositions (A1) and (B1) are indicated in Table 2 below.

TABLE 2

HC BLUE No 15 or Basic Blue 77

[Chemical structure with $H_2N$, $NH$, $Cl$, $Cl$, $H_3PO_4$]

BASIC VIOLET 2

[Chemical structure with $NH_2^{\oplus}$, $Cl^-$, $H_2N$, $NH_2$]

c. Procedure

Compositions A1 and B1 are applied to locks of hair that is very sensitized owing to bleaching, in a proportion of 5 g of composition per 1 g of hair.

After a leave-on time of 20 minutes at ambient temperature, the locks are rinsed with clear water, then dried.

d. Evaluation

The colorimetric measurements are performed using a Minolta CM2006D spectrocolorimeter (illuminant D65, angle 10°, specular component included) in the CIELab system.

e Results

The results are reported in Table 3 below.

TABLE 3

|  | L* |
|---|---|
| B1 - BV2 pH 3.5 | 30.90 |
| A1 - HB15 pH 3.5 | 28.18 |

The power is represented by the value of L*: the lower the value of L*, the more powerful the colour obtained.

As shown by the table above, the compositions according to the invention (A1 and B1) lead to powerful colours.

II. Example 2 a Compositions Tested

Compositions (C1), (C2) and (D) below were prepared from the ingredients as described below, the contents of which are indicated in gram % (unless otherwise mentioned) in Table 4 below.

TABLE 4

|  | C1 (invention) | C2 (invention) | D (comparative) |
|---|---|---|---|
| Sodium Hydroxide | pH = 3.5 | pH = 3.5 | pH = 3.5 |
| HC Blue No. 15 | 0.5 | — | — |
| Basic Blue 1 | — | 0.5 | — |
| Basic Blue 99 | — | — | 0.5 |
| Cetyl alcohol | 0.95 | 0.95 | 0.95 |
| Guar Hydroxypropyltrimonium Chloride | 0.1 | 0.1 | 0.1 |
| Cetearyl Alcohol | 3.75 | 3.75 | 3.75 |
| Preservative | qs | qs | qs |
| Amodimethicone | 1.15 | 1.15 | 1.15 |
| Behentrimonium Chloride | 2 | 2 | 2 |
| Citric acid | 0.025 | 0.025 | 0.025 |
| Hydroxyethylcellulose | 0.2 | 0.2 | 0.2 |
| Water | qs 100 | qs 100 | qs 100 |

Compositions (C1) and (C2) are compositions according to the invention, because the direct dye used corresponds to the claimed formula, unlike comparative composition (D).

e. Direct Dyes Tested

The direct dyes used in compositions (C1), (C2) and (D) are indicated in the table below:

HC Blue No 15

[Chemical structure with $H_2N$, $NH$, $Cl$, $Cl$, $H_3PO_4$]

-continued

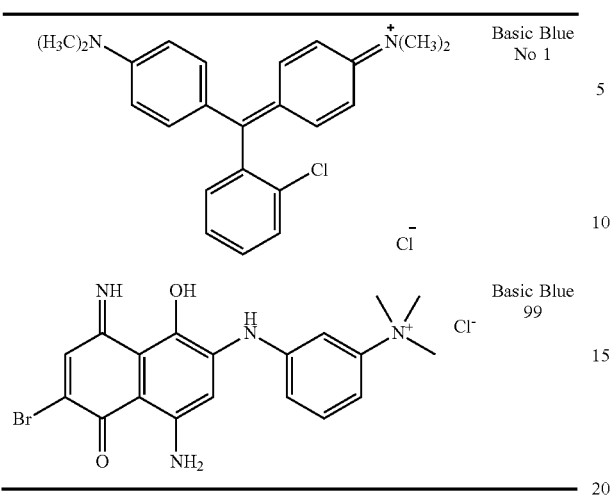

f. Procedure

Compositions C1, C2 and D are applied to locks of natural hair containing 90% grey hairs, in a proportion of 5 g per gram of hair.

After a leave-on time of 20 minutes at ambient temperature, the locks are rinsed with clear water, then dried.

g. Evaluation

The colorimetric measurements are performed using a Minolta CM2006D spectrocolorimeter (illuminant D65, angle 10°, specular component included) in the CIELab system.

h. Results

The results are reported in Table 5 below.

TABLE 5

|  | L* | a* | b* | ΔE |
|---|---|---|---|---|
| Non-dyed hair | 63.66 | 2.07 | 16.43 |  |
| C1 (invention) | 25.31 | 5.55 | −32.55 | 62.30 |
| C2 (invention) | 23.49 | −16.61 | −13.78 | 53.62 |
| D (comparative) | 21.24 | 1.24 | −7.46 | 48.96 |

Compositions C1 and C2 according to the invention result in a better buildup of the colour compared with comparative composition D.

The invention claimed is:

1. A composition for dyeing keratin fibres comprising, in a cosmetically acceptable medium:
   (i) at least one direct dye of triarylmethane structure,
   (ii) at least one amino silicone, and
   (iii) at least one surfactant;
   wherein the pH of the composition is acidic.

2. The composition according to claim 1, wherein the at least one direct dye of triarylmethane structure is chosen from the anionic, cationic, neutral or zwitterionic dyes of formula (I)

(I)

or the organic or mineral, acid or base addition salts thereof, the geometrical isomers, optical isomers or tautomers thereof, the mesomeric forms thereof, or the solvates or hydrates;
wherein in formula (I):
A, B and C are identical or different, and each represents a (hetero)aryl group which is optionally substituted, and
═ represents a single bond or a double bond.

3. The composition according to claim 1 wherein the at least one direct dye of triarylmethane structure is chosen from the cationic dyes of formulae (IIa) and (II'a) below:

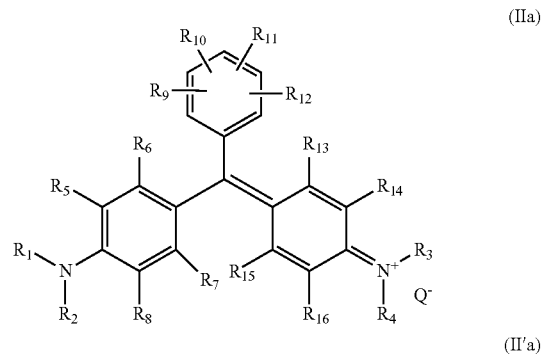

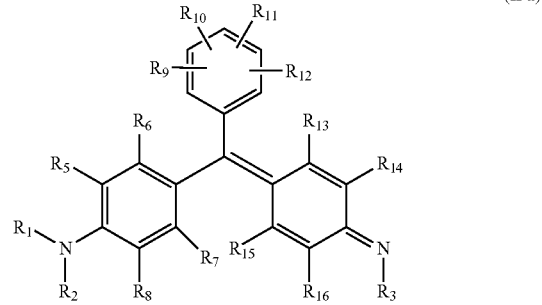

or the organic or mineral, acid or base addition salts thereof, the geometrical isomers, optical isomers or tautomers thereof, the mesomeric forms thereof, or the solvates or hydrates thereof;
wherein in formulae (IIa) and (II'a):
* R1, R2, R3 and R4, which may be identical or different, each represents a hydrogen atom or a ($C_1$-$C_6$)alkyl group which is optionally substituted with a hydroxyl group, an aryl group, phenyl, an aryl($C_1$-$C_4$)alkyl group, benzyl, a heteroaryl, or a heteroaryl($C_1$-$C_4$)alkyl group, or else two groups R1 and R2, and/or R3 and R4, borne by the same nitrogen atom, form, together with the nitrogen atom which bears them, an optionally substituted heterocycloalkyl group, morpholino, piperazino, or piperidino;
* R5, R6, R7, R8, R9, R10, R11, R12, R13, R14, R15, and R16, which may be identical or different, each represents a hydrogen atom, a halogen atom, or a group chosen from i) hydroxyl; ii) thiol; iii) amino; iv) (di)($C_1$-$C_4$)(alkyl)amino; v) (di)arylamino or (di)phenylamino; vi) nitro; vii) acylamino (—NR—C(O)R') in which the radical R is a hydrogen atom or a $C_1$-$C_4$ alkyl radical optionally bearing at least one hydroxyl group, and the radical R' is a $C_1$-$C_2$ alkyl radical; viii) carbamoyl ((R)2N—C(O)—) in which the radicals R, which may be identical or different, represent a hydrogen atom or a $C_1$-$C_4$ alkyl radical optionally bearing at least one hydroxyl group; ix) carboxylic acid or ester, (—O—C(O)R') or (—C(O)OR'), in which the radical R' is a hydrogen atom, or $C_1$-$C_4$ alkyl optionally bearing at least one hydroxyl group and the radical R' is a $C_1$-$C_2$ alkyl radical; x) alkyl optionally substituted with a hydroxyl group; xi) alkylsulfonylamino (R'SO$_2$—NR—) in which the radical R represents a hydrogen atom or a $C_1$-$C_4$alkyl radical optionally bearing at least one hydroxyl group and the radical R' represents a $C_1$-$C_4$ alkyl radical or a phenyl radical; xii) aminosulfonyl ((R)2N—SO$_2$_) in which the radicals R, which may be identical or different, represent a hydrogen atom or a $C_1$-$C_4$ alkyl radical optionally bearing at least one hydroxyl group; xiii) ($C_1$-$C_4$)alkoxy; or xiv) ($C_1$-$C_4$) alkylthio;
* or else two radicals borne by two contiguous carbon atoms R5 and R6 and/or R7 and R8 and/or R9 and R10 and/or R11 and R12 and/or R13 and R14 and/or R15 and R16 form, together with the carbon atoms which bear them, an aryl or heteroaryl, said ring being optionally substituted;
* Q- represents an anionic counterion for achieving electroneutrality.

4. The composition according to claim 1, wherein the at least one direct dye of triarylmethane structure is chosen from those of formula (IIa) or (II'a), wherein, taken together or separately:
R1, R2, R3 and R4 each represents a hydrogen atom, a ($C_1$-$C_4$)alkyl group methyl, or ethyl,
R5, R6, R7, R8, R9, R10, R11, R12, R13, R14, R15, and R16 each represents a hydrogen atom, a halogen atom, chlorine, a ($C_1$-$C_4$)alkyl group methyl, ethyl, an amino group, or a (di)($C_1$-$C_4$)(alkyl)amino group.

5. The composition according to claim 1, wherein the at least one direct dye of triarylmethane structure is chosen from Basic Violet 1, Basic Violet 2, Basic Violet 3, Basic Violet 4, Basic Violet 14, Basic Blue 1, Basic Blue 7, Basic Blue 26, Basic Green 1, Basic Blue 77, or mixtures thereof.

6. The composition according to claim 1, wherein the total amount of the at least one direct dye of triarylmethane structure ranges from 0.0001% to 10% by weight, relative to the total weight of the composition.

7. The composition according to claim 1, wherein the composition further comprises at least one amino silicone, chosen from the silicones of formula (B) below:

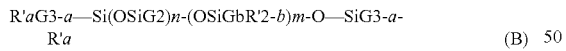

R'aG3-a—Si(OSiG2)n-(OSiGbR'2-b)m-O—SiG3-a-R'a    (B)

wherein:
G, which may be identical or different, represents a hydrogen atom or a phenyl, OH, $C_1$-$C_8$ alkyl, methyl, $C_1$-$C_8$ alkoxy, or methoxy group,
a, which may be identical or different, represents 0 or an integer from 1 to 3,
b denotes 0 or 1,
m and n are numbers such that the sum (n+m) ranges from 1 to 2000, wherein n represents a number from 0 to 1999, and m represents a number from 1 to 2000;
R', which may be identical or different, represents a monovalent radical of formula -CqH2qL in which q is a number ranging from 2 to 8 and L is an optionally quaternized amino group chosen from —N(R")2; —N+(R")3 A-; —R"-Q-N(R")2, or —NR"-Q-N+(R")3 A-, wherein:
R", which may be identical or different, represents hydrogen, phenyl, benzyl, a saturated monovalent hydrocarbon-based radical, or a $C_1$-$C_{20}$ alkyl radical;
Q denotes a linear or branched CrH2r group, r being an integer ranging from 2 to 6; and
A- represents a cosmetically acceptable anion, a halide, fluoride, chloride, bromide, or iodide.

8. The composition according to claim 7, wherein the at least one amino silicone is chosen from the silicones of formula (F) below:

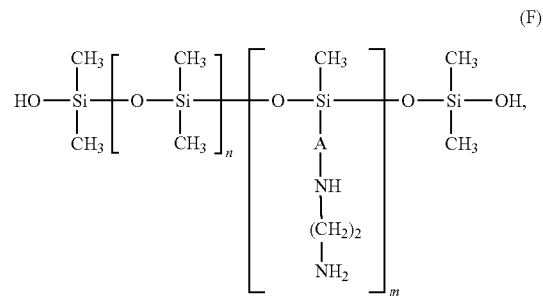

wherein:
m and n are numbers such that the sum (n+m) ranges from 1 to 2000, wherein n represents a number from 0 to 1999, and m represents a number from 1 to 2000;
A denotes a linear or branched, alkylene radical containing from 4 to 8 carbon atoms.

9. The composition according to claim 7, wherein the total amount of the amino silicone ranges from 0.01% to 10% by weight, relative to the total weight of the composition.

10. The composition according to claim 1, wherein the at least one surfactant is a cationic surfactant.

11. The composition according to claim 10, wherein the cationic surfactant is chosen from cetyltrimethylammonium, behenyltrimethylammonium, dipalmitoylethylhydroxyethylmethylammonium salts, or mixtures thereof.

12. The composition according to claim 1, further comprising at least one fatty substance in a total amount of greater than or equal to 3% by weight, relative to the total weight of the composition.

13. The composition according to claim 1, further comprising at least one additive chosen from a thickening polymer, a cationic polymer, an additional direct dye, or a mixture thereof.

14. A process for dyeing keratin fibres, the process comprising applying to said fibres a composition comprising, in a cosmetically acceptable medium:
(i) at least one direct dye of triarylmethane structure,
(ii) at least one amino silicone, and
(iii) at least one surfactant;
wherein the pH of the composition is acidic.

15. A process for dyeing human hair, the process comprising applying to said hair a composition comprising, in a cosmetically acceptable medium:
(i) at least one direct dye of triarylmethane structure,
(ii) at least one amino silicone, and
(iii) at least one surfactant;
wherein the pH of the composition is acidic.

16. The composition according to claim 11, wherein the cationic surfactant is chosen from behenyltrimethylammonium chloride, cetyltrimethylammonium chloride, dipalmitoylethyl-hydroxyethylmethylammonium methosulfate, or mixtures thereof.

* * * * *